US012642458B2

(12) United States Patent
Lee et al.

(10) Patent No.: US 12,642,458 B2
(45) Date of Patent: Jun. 2, 2026

(54) GLUCOSE DETECTING COMPLEX AND CONTACT LENS-TYPE SENSOR COMPRISING SAME FOR DETECTING GLUCOSE IN TEARS

(71) Applicant: INDUSTRY-UNIVERSITY COOPERATION FOUNDATION HANYANG UNIVERSITY, Seoul (KR)

(72) Inventors: Dong Yun Lee, Seoul (KR); Woori Bae, Seoul (KR); Sijin Park, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 820 days.

(21) Appl. No.: 17/725,353

(22) Filed: Apr. 20, 2022

(65) Prior Publication Data

US 2022/0248990 A1 Aug. 11, 2022

Related U.S. Application Data

(63) Continuation-in-part of application No. 16/337,341, filed as application No. PCT/KR2017/010680 on Sep. 27, 2017, now abandoned.

(30) Foreign Application Priority Data

Sep. 28, 2016 (KR) ........................ 10-2016-0124660

(51) Int. Cl.
| | |
|---|---|
| *A61B 5/145* | (2006.01) |
| *A61B 3/10* | (2006.01) |
| *A61B 5/00* | (2006.01) |

(52) U.S. Cl.
CPC ...... *A61B 5/14532* (2013.01); *A61B 5/14507* (2013.01); *A61B 3/101* (2013.01); *A61B 5/6821* (2013.01)

(58) Field of Classification Search
CPC . A61B 5/14532; A61B 5/14507; A61B 3/101; A61B 5/6821; C12Q 1/54;
(Continued)

(56) References Cited

U.S. PATENT DOCUMENTS

| 2004/0114101 A1* | 6/2004 | Thakrar | ................. G02C 7/046 |
| | | | 351/159.66 |
| 2007/0016074 A1 | 1/2007 | Abreu | |

(Continued)

FOREIGN PATENT DOCUMENTS

KR 10-2008-0109328 W 12/2008

OTHER PUBLICATIONS

Kang, et al. "Fabrication of conductive oxidase-entrapping nanocomposite of mesoporous ceria-carbon for efficient electrochemical biosensor" RSC Adv., vol. 5, pp. 78747-78753 (2015).
(Continued)

*Primary Examiner* — David W Berke-Schlessel
*Assistant Examiner* — Trent R Clarke
(74) *Attorney, Agent, or Firm* — NKL Law; Jae Youn Kim

(57) ABSTRACT

The present invention relates to a glucose detecting complex and a contact lens-type sensor comprising the same for detecting glucose in tears. The contact lens-type sensor for detecting glucose according to the present invention includes a complex in which glucose oxidase is coupled to cerium oxide nanoparticles. Such a configuration allows the visualization of changes in glucose concentrations and the quantitative measured of glucose in a simpler and more economical way. In addition, glucose concentrations can be
(Continued)

monitored in real time through a non-invasive method by measuring the concentration of glucose in tears rather than in blood in comparison with the conventional blood glucose measurement method. Therefore, the present invention can be widely applied in the technical field for the early diagnosis and prevention of diabetes.

8 Claims, 45 Drawing Sheets

(58) Field of Classification Search
CPC ............. C12Q 1/006; G01N 2333/904; G01N 2800/042; G01N 2800/50; G02C 7/04
See application file for complete search history.

(56) References Cited

U.S. PATENT DOCUMENTS

| | | |
|---|---|---|
| 2010/0113901 A1 | 5/2010 | Zhang et al. |
| 2012/0245444 A1 | 9/2012 | Otis et al. |
| 2012/0259188 A1 | 10/2012 | Besling |
| 2014/0220608 A1 | 8/2014 | Andreescu et al. |
| 2015/0118316 A1* | 4/2015 | Seal .................... A61K 47/6935 |
| | | 424/490 |
| 2015/0230737 A1 | 8/2015 | Heller |
| 2018/0356404 A1 | 12/2018 | Strano et al. |

OTHER PUBLICATIONS

Ornatska et al., "Paper Bioassay Based on Ceria Nanoparticles as Colorimetric Probes", Anal. Chem. 2011, 83:4273-4280.
Steiner et al., "Optical methods for sensing glucose", Chem. Soc. Rev., 2011, 40, 4805-4839.
Thermo Fisher Scientific; "Chemistry of Corsslinking", websited accessed at https://www.thermofisher.com/us/en/home/life-science/protein-biology/protein-biology-learning-center/protein-biology-resource-library/pierce-protein-methods/chemistry-crosslinking.html on Mar. 24, 2021. (Year: 2021).
Yao et al., "A contact lens with embedded sensor for monitoring tear glucose level", Biosensors and Bioelectronics 26(2011) 3290-3296.

* cited by examiner

| Samples | CeNP-PEG-GOx |
| --- | --- |
| Amount of enzyme conjugated | 248.17 μg-protein/ml |

| Name | Peak BE | FWHM | Area | At % |
|------|---------|------|------|------|
| O1s | 529.72 | 2.96 | 26849.37 | 62.24 |
| Ce3d | 882.58 | 4.62 | 217720.12 | 37.76 |

H₂O₂ (immediately, RT)

CeO₂ nanoparticle: 1 w/v %

Glucose (Glucose oxidase : 100.12 U/ml) (2 min, RT)

0 mM     0.5 mM     1 mM     2.5 mM     5 mM $CeO_2$ nanoparticle: 1 w/v %

$y = -51.717x + 89.805$
$R^2 = 0.98362$

GLUCOSE (immediately, RT, mM)

CNP-PEG-GOX (µg/lens)

CeO₂ nanoparticle solution

CNP-PEG-GOX lens in buffer
(after 1 month)

Only buffer
(before adding CNP-PEG-GOX lens)

Before wearing

After wearing

Glucose (mM)

| 0 | 0.2 | 0.4 | 0.6 | 1.2 |

$y = -0.0091x + 0.3405$
$R^2 = 0.9415$

| | blood glucose level (mg/dl) | tear glucose level (mM)) |
|---|---|---|
| Normal | 141 | 0.378152 |
| Diabetic | 540 | 1.818213 |

Tear glucose assay
by Finger-prick test

1

GLUCOSE DETECTING COMPLEX AND CONTACT LENS-TYPE SENSOR COMPRISING SAME FOR DETECTING GLUCOSE IN TEARS

CROSS-REFERENCE TO RELATED APPLICATIONS

This application is a continuation in part of U.S. application Ser. No. 16/337,341, entitled "GLUCOSE DETECT-ING COMPLEX AND CONTACT LENS-TYPE SENSOR COMPRISING SAME FOR DETECTING GLUCOSE IN TEARS", filed Mar. 27, 2019, which claims priority to and is a 35 U.S.C. § 371 national phase application of PCT/KR2017/010680 (WO2018/062830), filed on Sep. 27, 2017 entitled "GLUCOSE DETECTING COMPLEX AND CON-TACT LENS-TYPE SENSOR COMPRISING SAME FOR DETECTING GLUCOSE IN TEARS", which application claims priority to and the benefit of Korean Patent Appli-cation No. 10-2016-0124660, filed Sep. 28, 2016; the dis-closures of which are incorporated herein by reference in their entirety

TECHNICAL FIELD

The present invention relates to a composite for detecting glucose and a contact lens-type sensor for detecting glucose in tears, which includes the same.

BACKGROUND ART

Diabetes is a serious disease which occurs in one of 19 persons worldwide, and according to a report of the Credit Suisse Research Institute, approximately 400 million patients in the world are suffering from type II diabetes, and the number of patients is gradually increasing. In Korea, due to a great increase in the incidence of chronic diseases such as diabetes caused by the progression of aging, a change in eating habits and an increase in life expectancy, the burden of medical expenses on individuals and society is increasing. One of the methods for preventing and minimizing type II diabetes and complications caused thereby (e.g., myocardial infarction, stroke, retinopathy, renal failure, etc.) is a method for usually and continuously self-monitoring a blood glu-cose level, and in fact, diabetic patients are measuring their blood glucose levels several times a day and monitoring their biological changes caused by diabetes.

As a conventional method, there is a method for applying blood taken by pricking a fingertip with a needle to measure a blood glucose level using a glucometer, but this method has not been widely used due to inconvenience of several measurements and an increased pain of pricking, despite its necessity for maintaining the health of a patient. In other words, since diabetic patients have a strong repulsion to a user interface/user experience (UI/UX)-type glucometer with such inconvenience, the development of non-invasive, continuous and self-monitoring technology for easily detect-ing glucose in the body is urgently required.

Today, most biosensors for detecting glucose have used glucose oxidase as a material for recognizing glucose. However, the conventional sensors have used, as a method for calculating a glucose concentration, a method for directly measuring oxygen consumption, the productivity of hydro-gen peroxide or a pH change; a method for detecting a change in electrical signal produced by an enzyme reaction through cyclic voltammetry; and a method for detecting an optical change induced by a secondary reaction between a product and a fluorescent material through fluorescence resonance energy transfer (FRET), but there is a disadvan-tage that these methods need additional apparatuses. More-over, potentiometry or amperometry has been applied to most of the recently noticeable "smart contact lens" tech-nologies, and various types of control circuits, communica-tion circuits and antennae for realizing the "smart" functions should be fabricated in an ultra-small size, and therefore it is required to develop additional technology related to the smart technology for commercialization.

Because of this, as a way to diagnose and prevent diabe-tes, studies on non-invasive and simpler techniques for measuring a blood sugar or glucose level are actively progressing (Korean Unexamined Patent Application No. 10-2008-0109328), but have achieved little.

DISCLOSURE

Technical Problem

The present invention is suggested to solve the above-mentioned problems, and the inventors could more easily detect glucose by a colorimetric reaction with cerium oxide using a complex including glucose oxidase conjugated to cerium oxide nanoparticles, and based on the result, detected glucose in tears using a contact lens-type sensor of the present invention, which includes the complex, thereby confirming that the glucose in tears can be simply and non-invasively detected. Accordingly, the present invention was completed.

Therefore, the present invention is directed to providing a contact lens-type sensor for detecting glucose, which includes a complex for detecting glucose in tears.

The present invention is also directed to providing a complex for detecting glucose, which includes cerium oxide ($CeO_2$) nanoparticles and glucose oxidase.

The present invention is also directed to providing a novel use of the complex for detecting glucose.

However, technical problems to be solved in the present invention are not limited to the above-described problems, and other problems which are not described herein will be fully understood by those of ordinary skill in the art from the following descriptions.

Technical Solution

One aspect of the present invention provides a contact lens-type sensor for detecting glucose, which includes a complex for detecting glucose, which includes cerium oxide nanoparticles and glucose oxidase.

According to an exemplary embodiment of the present invention, the complex may include cerium oxide nanopar-ticles, a biocompatible polymer, and glucose oxidase, which are sequentially conjugated, wherein the biocompatible polymer may be selected from the group consisting of polyethylene glycol (PEG), poly(acrylamide) (PAM), poly (allylamine) (PAL), poly(ethyleneimine) (PEI), poly(amido-amine) (PAMAM), polylysine (PL), poly(lactide) (PLA), poly(acrylic acid) (PAA), poly(N-isopropylacrylamide) (PNIPAM), poly(2-(dimethyl-amino)ethyl methacrylate) (PDMAEMA), poly(caprolactone) (PCL), chitosan, poly(N-vinyl caprolactam) (PVCL), dextran, poly(styrene sulfonate) (PSS) and poly(vinylsulfonic acid) (PVSA), and the sequen-tial conjugation between the cerium oxide nanoparticles, the biocompatible polymer and the glucose oxidase may be made by a covalent bond, and more specifically, an amide bond.

According to another exemplary embodiment of the present invention, a concentration of the cerium oxide nanoparticles may be 0.1 to 0.6 w/v % with respect to the total volume of the complex.

According to an exemplary embodiment of the present invention, the complex may be entrapped in the biocompatible polymer.

According to another exemplary embodiment of the present invention, a monomer of the biocompatible polymer may be selected from the group consisting of 2-hydroxyethyl methacrylate (HEMA), N-vinyl pyrrolidone (NVP), methacrylate (MMA), methyl methacrylate (MMA), and vinyl pyrrolidone (VP).

According to still another exemplary embodiment of the present invention, the complex may be included at 0.3 to 2.5 wt % (w/v) with respect to the total volume of the contact lens-type sensor.

Still another aspect of the present invention provides: a composition for detecting glucose, which includes the nanoparticle complex; a use of the complex for detecting glucose; and a method for detecting glucose, which includes administering the complex to a subject.

Yet another aspect of the present invention provides: a use of the contact lens-type sensor for detecting glucose; and a method for detecting glucose, which includes administering the contact lens-type sensor to a subject or treating a subject therewith.

Advantageous Effects

A contact lens-type sensor for detecting glucose according to the present invention can include a complex in which glucose oxidase is conjugated to cerium oxide nanoparticles, and due to this configuration, a change in glucose concentration can be visualized by a simpler and economical method, and quantitatively measured. In addition, compared with a conventional glucose detection method, the contact lens-type sensor can measure a glucose level in tears, rather than in blood, thereby monitoring a glucose concentration in real time in a non-invasive way. For this reason, the contact lens-type sensor can be widely applied to a technical field for early diagnosis and prevention of diabetes.

Figure 13A:
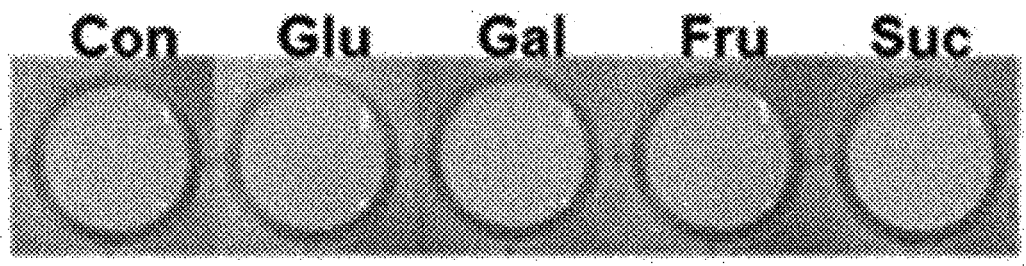
Figure 13B:
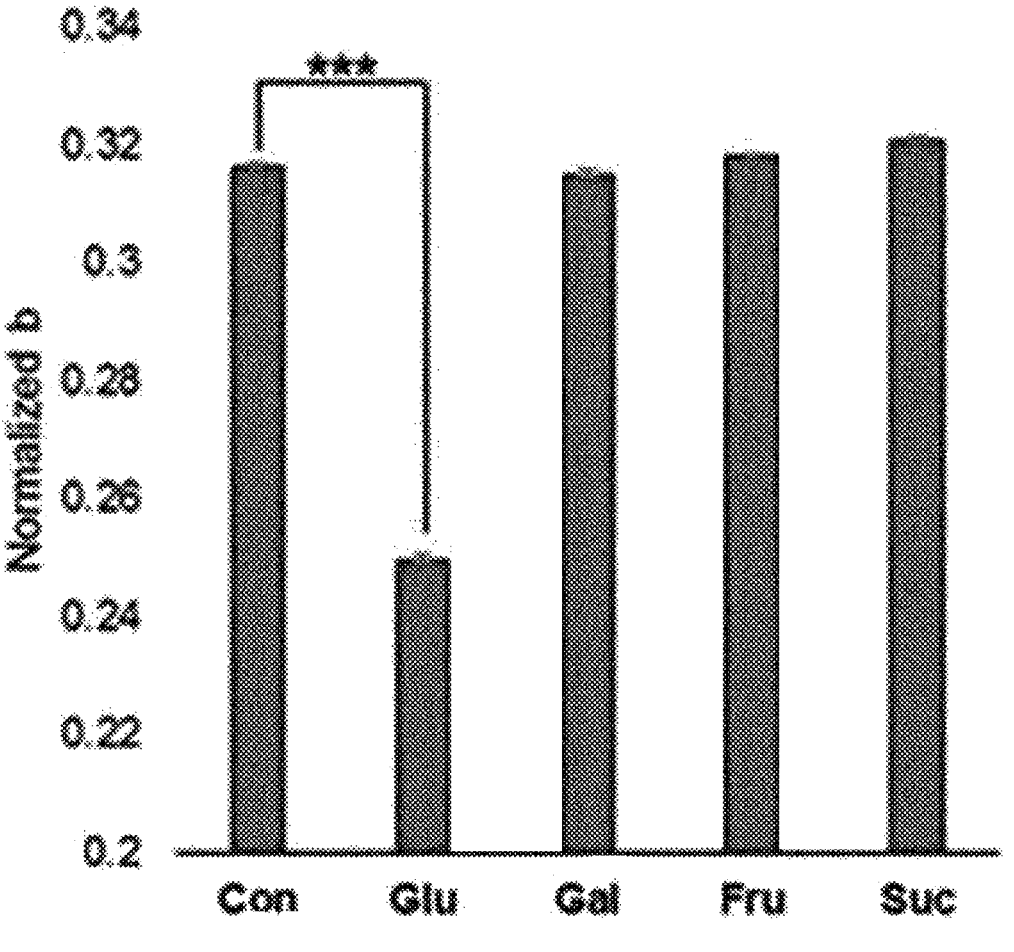

FIG. 13A shows a visual observation result of detecting a colorimetric reaction and FIG. 13B shows a result of color intensity analysis (RGB values) after a complex for detecting glucose according to the present invention is treated with various types of carbohydrates (fructose, galactose and sucrose).

Figure 14A:
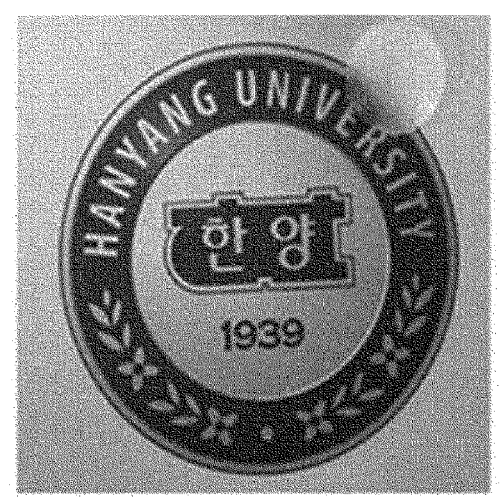

FIG. 14A shows a visual observation result of a contact lens-type sensor for detecting glucose according to the present invention.

Figure 14A:
Figure 14B:
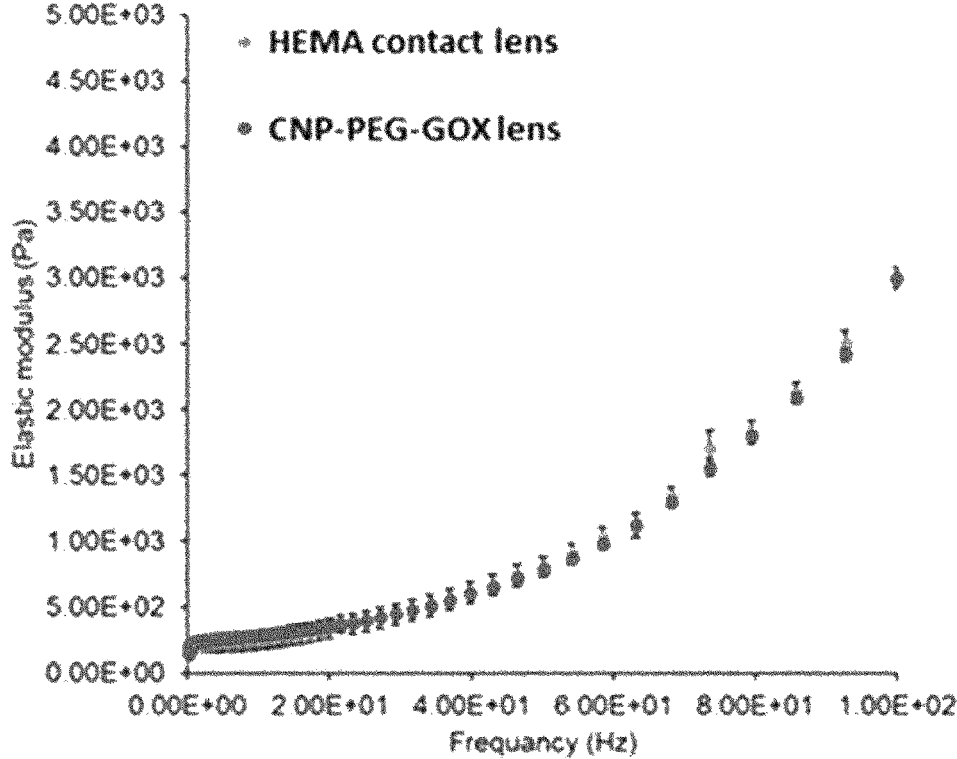

FIG. 14B shows a result of comparing a change in elasticity of a contact lens-type sensor for detecting glucose according to the present invention with that of a pHEMA contact lens.

Figure 15A:
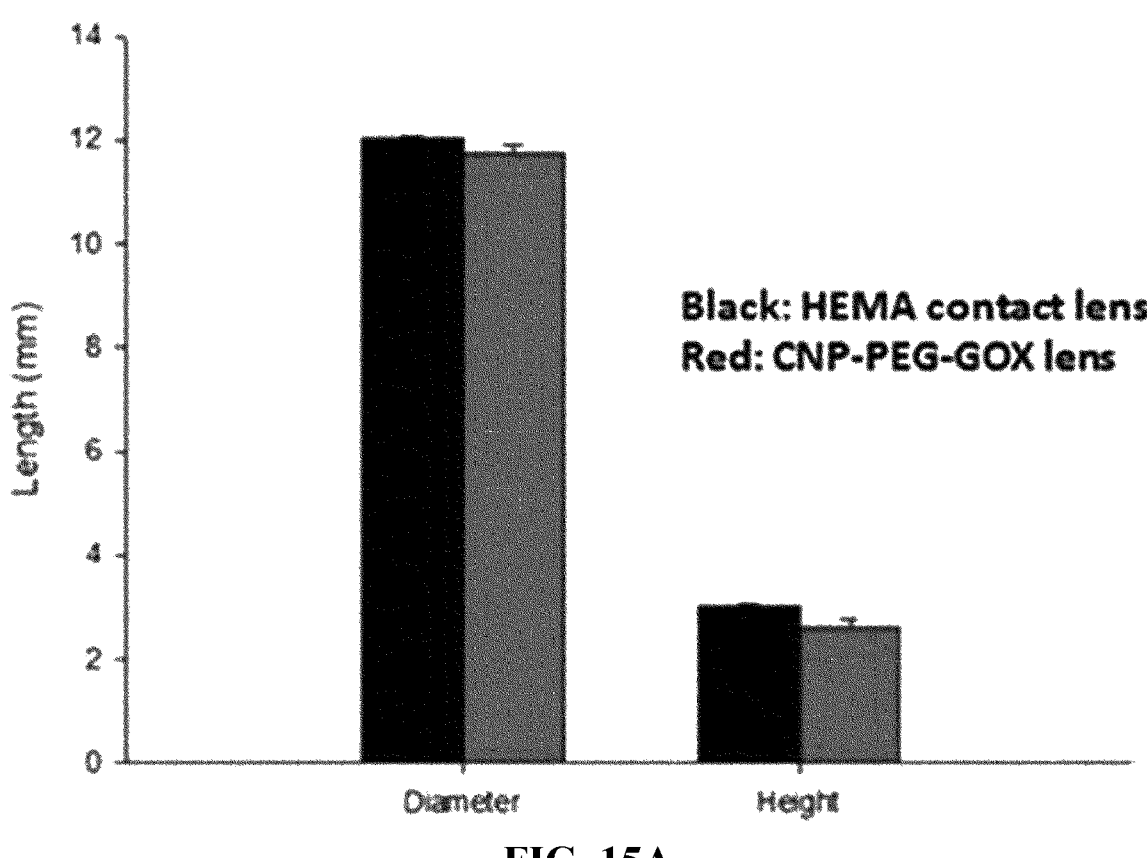

FIG. 15A shows a result of comparing a diameter and height before drying between a contact lens-type sensor for detecting glucose according to the present invention and a general pHEMA contact lens.

Figure 15B:
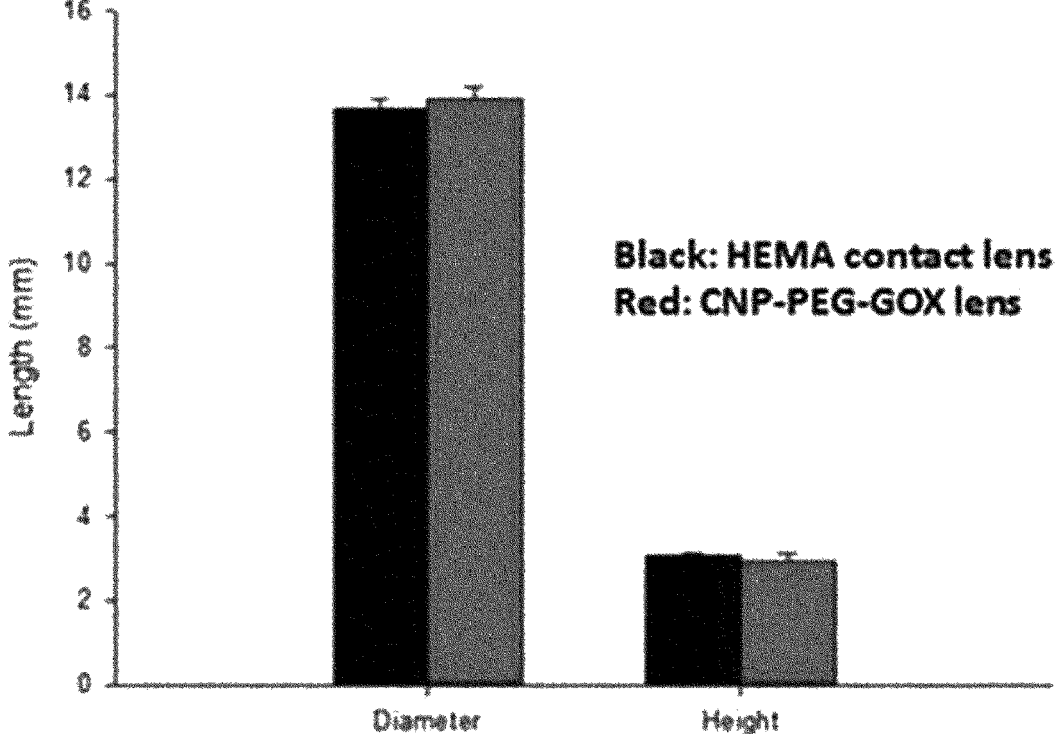

FIG. 15B shows a result of comparing a diameter and height after drying between a contact lens-type sensor for detecting glucose according to the present invention and a general pHEMA contact lens.

Figure 16:
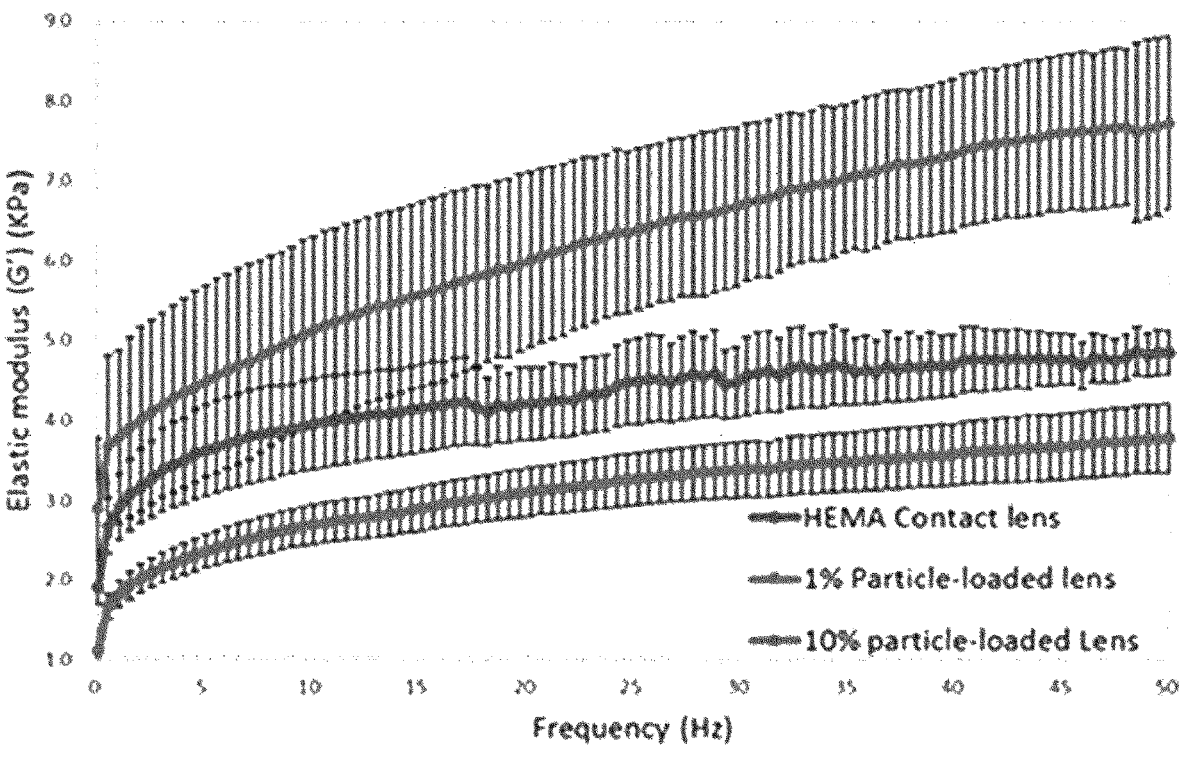

FIG. 16 shows a result of measuring a change in elastic modulus according to a concentration (1 or 10 wt/v %) of a complex for detecting glucose in a contact lens-type sensor for detecting glucose according to the present invention.

Figure 17A:
Figure 17B:
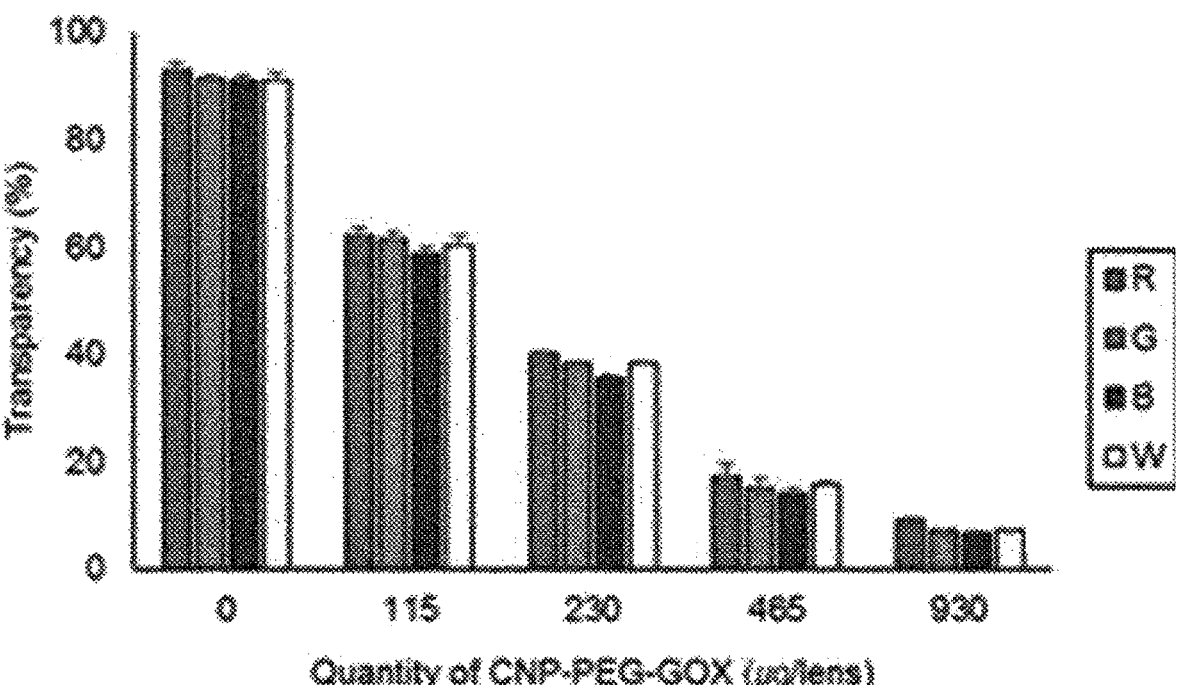

FIG. 17A shows a visual observation result and FIG. 17B shows a color intensity analysis (RGB values) confirming a change in transparency of a contact lens-type sensor according to the content (115, 230, 465 or 930 µg/lens) of a $CeO_2$-PEG-GOx complex.

Figure 18:
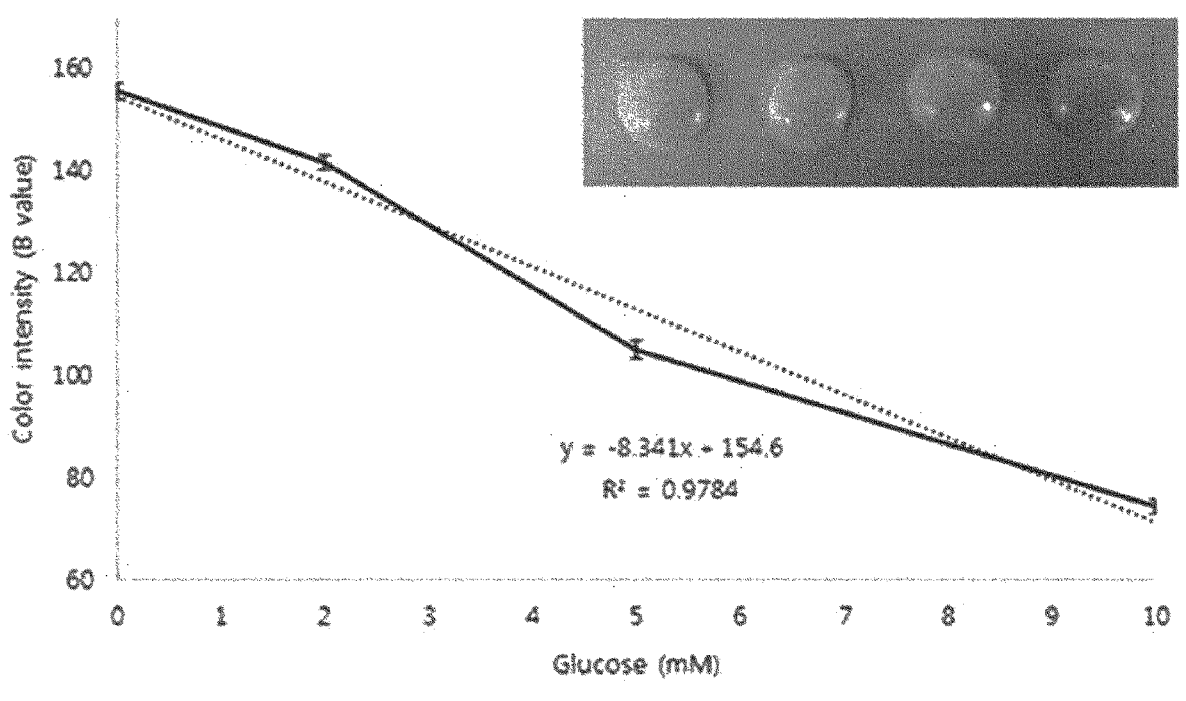

FIG. 18 shows a visual observation result of detecting a colorimetric reaction and a result of RGB color intensity analysis (B value) after a contact lens-type sensor for detecting glucose according to the present invention reacts with various concentrations (1 to 10 mM) of glucose in a buffer solution.

Figure 19:
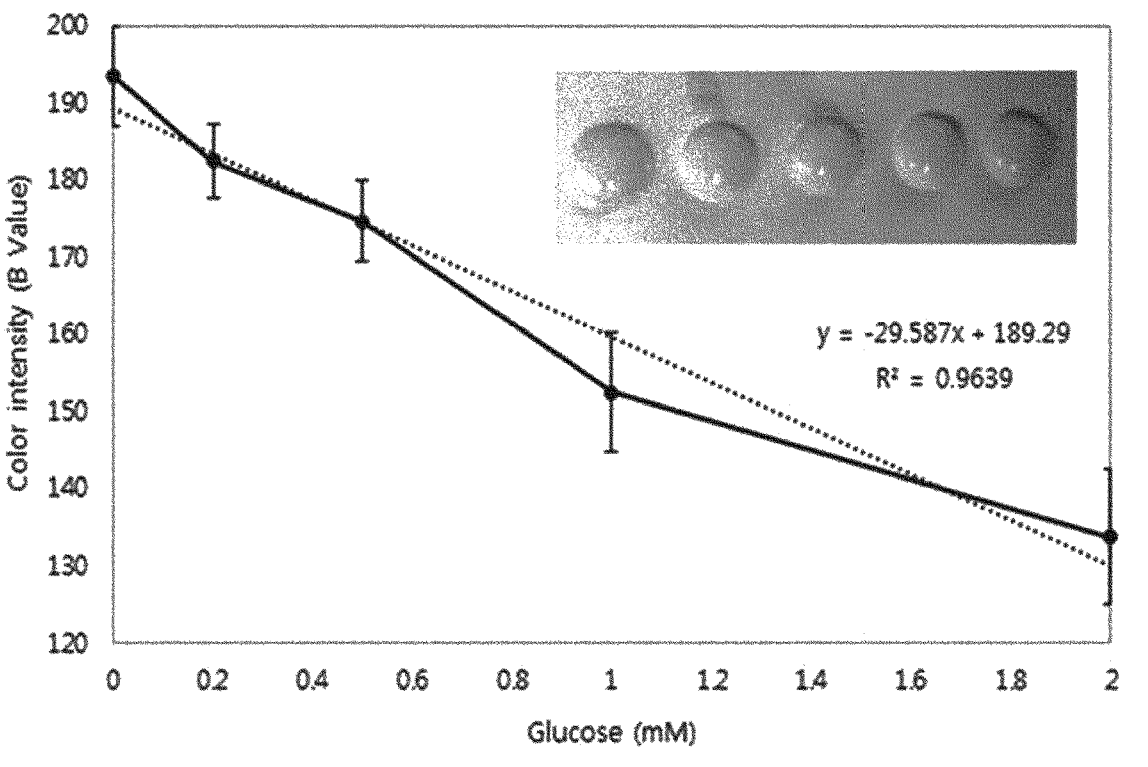

FIG. 19 shows a visual observation result of detecting a colorimetric reaction and a result of color intensity analysis (B value) after a contact lens-type sensor for detecting glucose according to the present invention reacts with various concentrations of glucose (0.2 to 2 mM) in artificial tears.

Figure 20A:
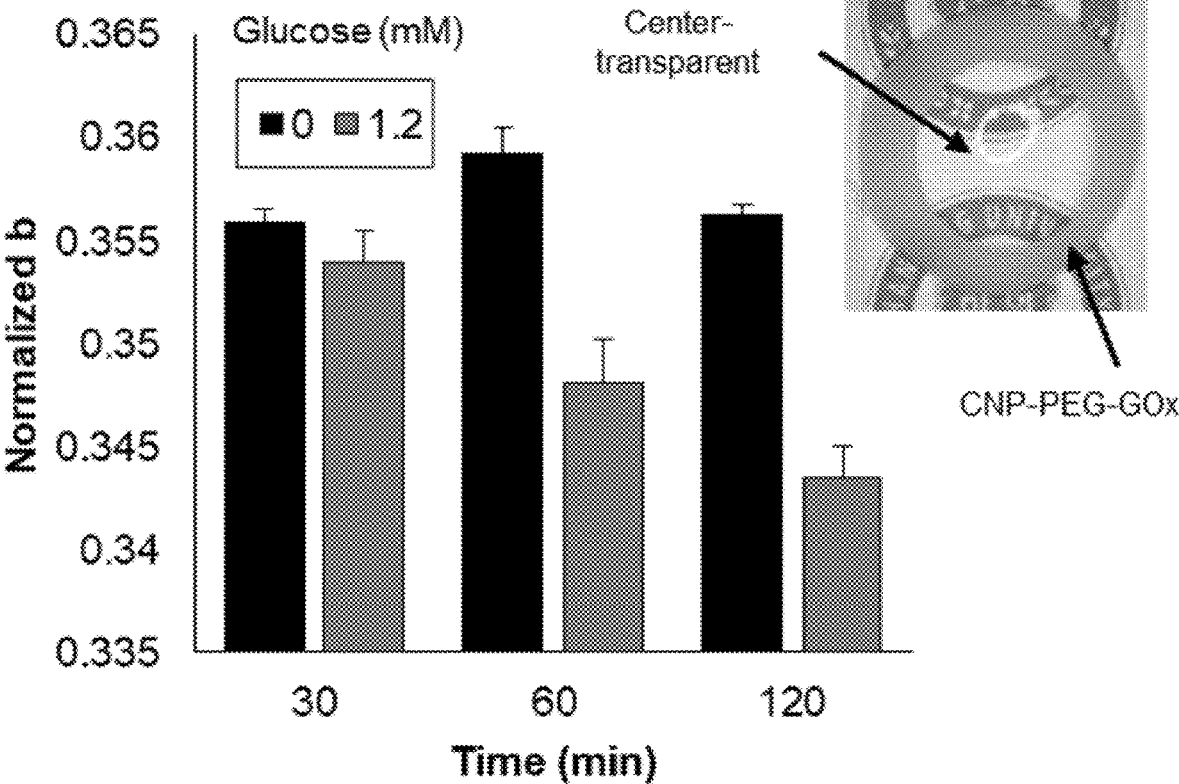

FIG. 20A shows a normalized b color profile of the center-transparent contact lenses with CNP-PEGGOx (930 µg/lens) (inset photograph) after treatment with glucose.

Figure 20B:
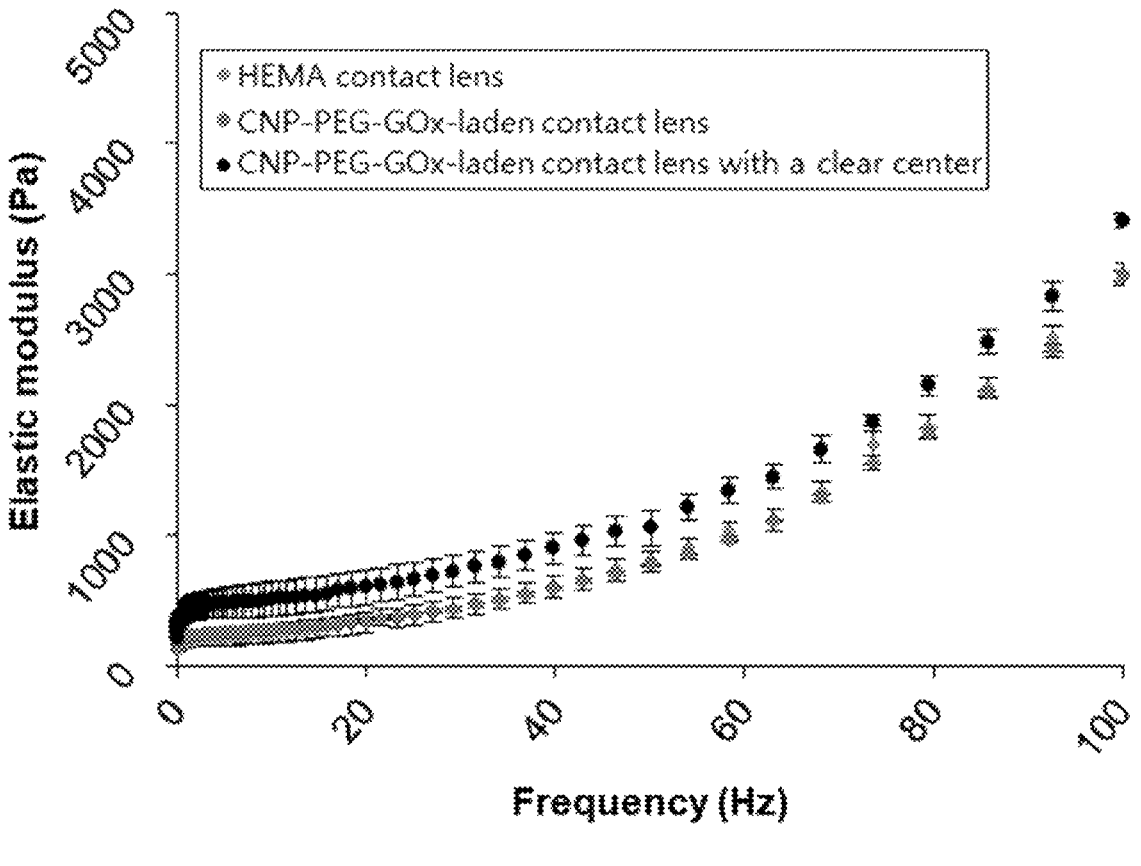

FIG. 20B shows a result of measuring an elastic modulus of the CNP-PEG-GOx-laden contact lenses (930 µg/lens), center-transparent contact lenses with CNP-PEG-GOx, and HEMA contact lenses without CNP-PEG-GOx (control group).

Figure 21A:
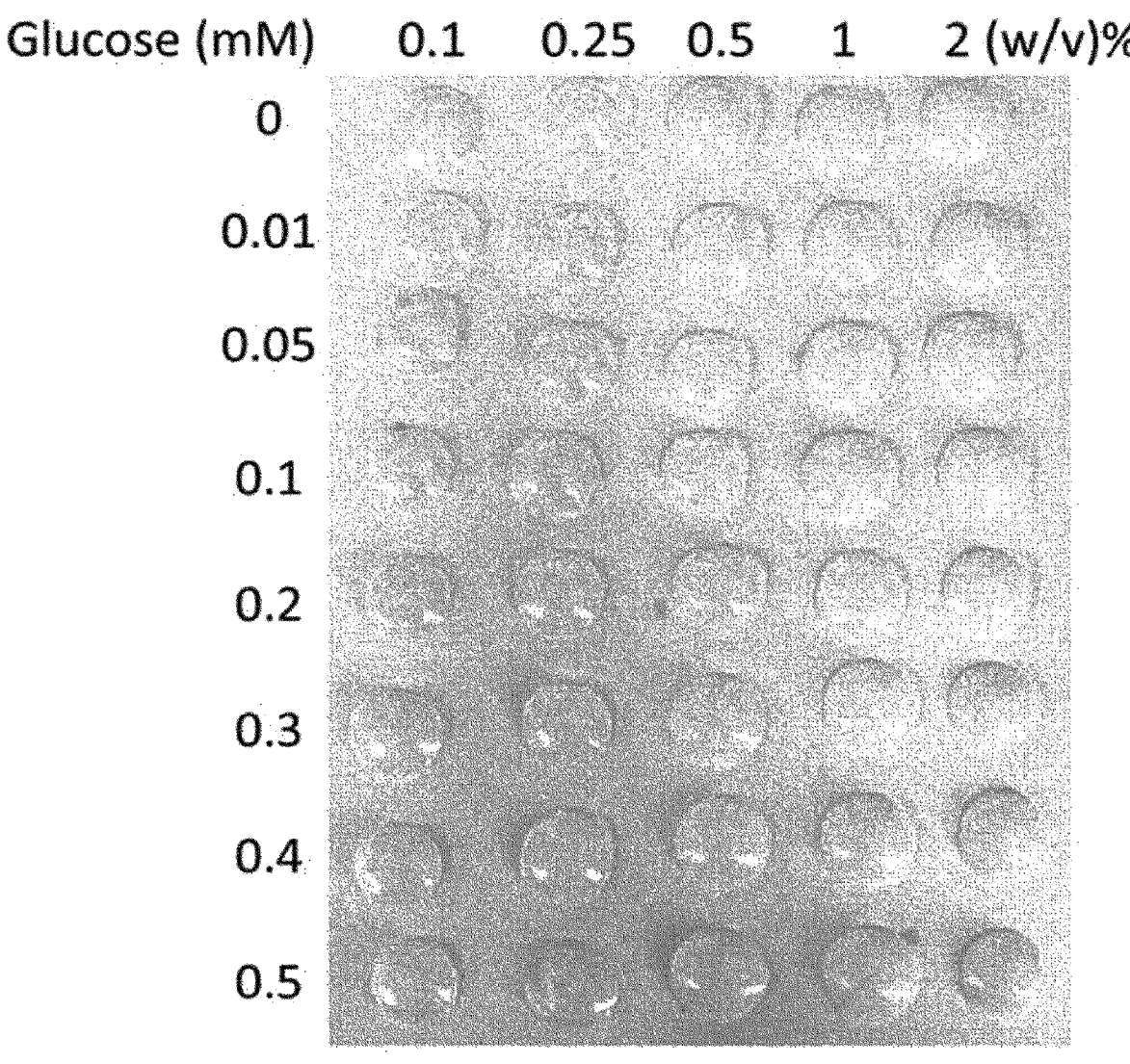

FIG. 21A shows a visual observation result of detecting a color change in a sensor per glucose concentration (0.01 mM to 0.5 mM) according to a concentration (0.1, 0.25, 0.5, 1 or 2% (w/v)) of a complex for detecting glucose in the contact lens-type sensor for detecting glucose according to the present invention.

Figure 21B:
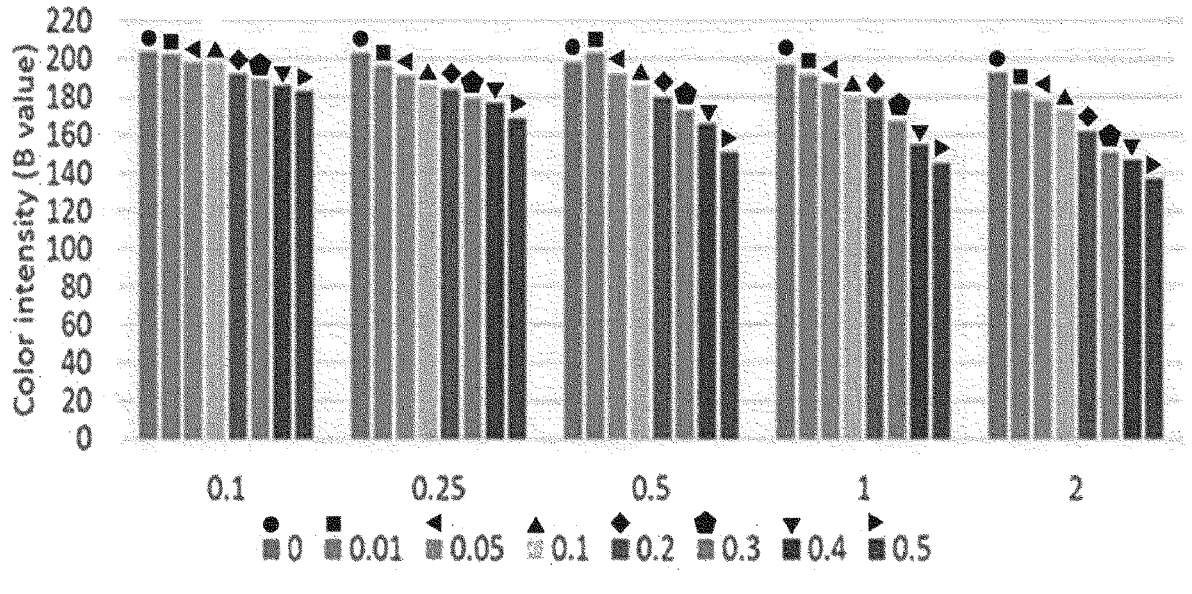

FIG. 21B shows a quantitative analysis result (B value) for a color change in a sensor per glucose concentration (0.01 mM to 0.5 mM) according to a concentration of a complex for detecting glucose (0.1, 0.25, 0.5, 1 or 2% (w/v)) in the contact lens-type sensor for detecting glucose according to the present invention.

Figure 22A:
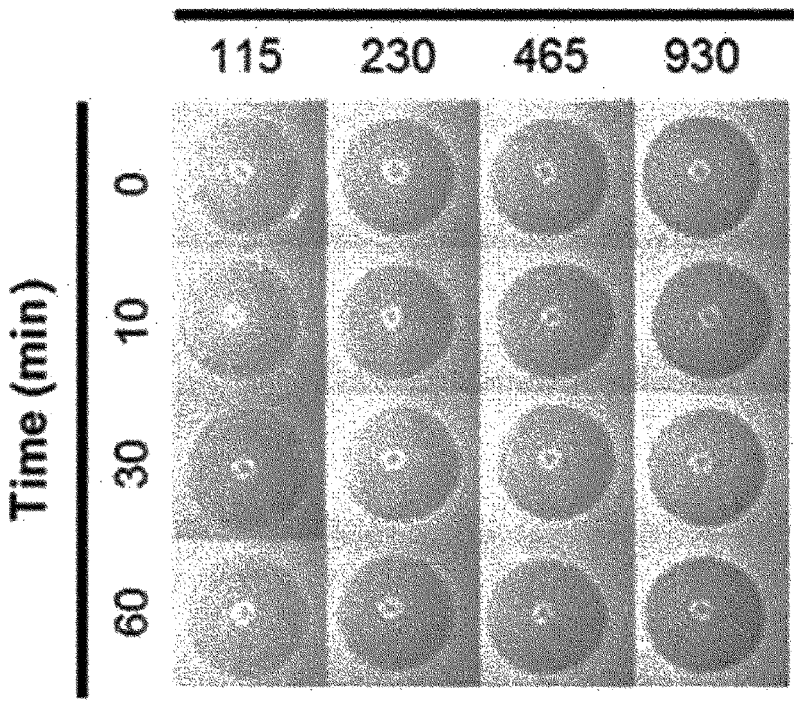

FIG. 22A shows a visual observation result of detecting a color change over time after a contact lens-type sensor for detecting glucose, including various contents (115, 230, 465 or 930 µg/lens) of a complex for detecting glucose, reacts with a constant concentration of glucose (0.6 mM).

Figure 22B:
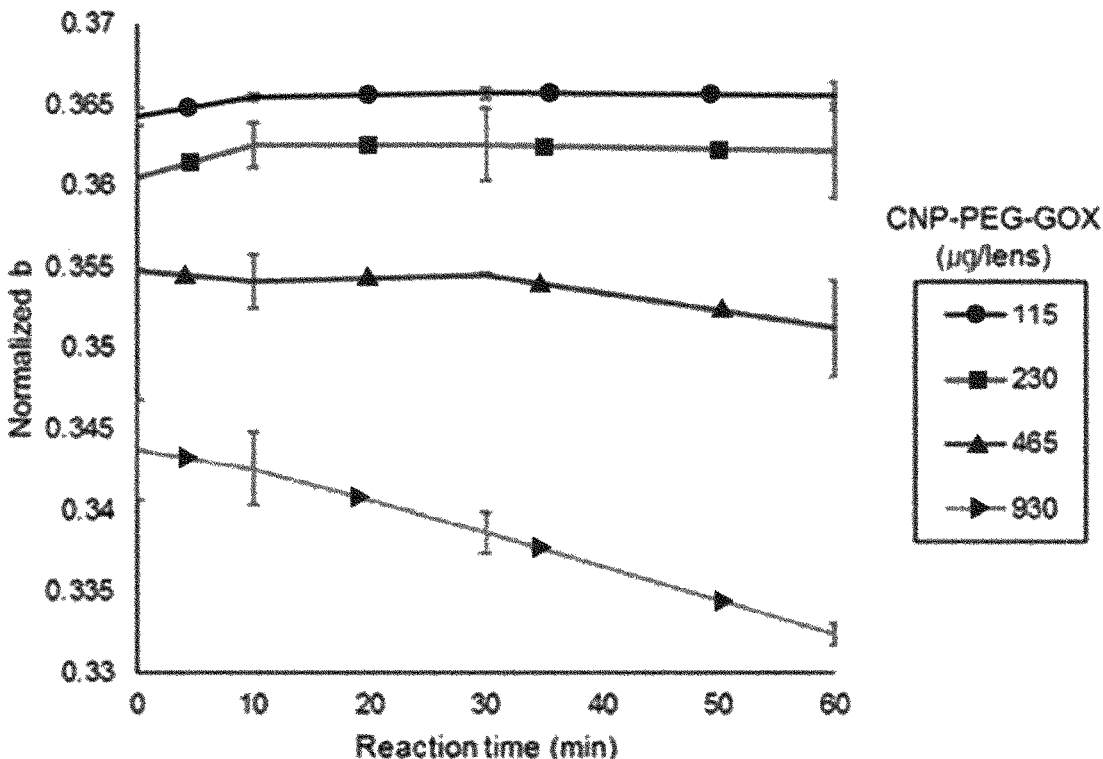

FIG. 22B shows a color intensity analysis (RGB values) result over time after a contact lens-type sensor for detecting glucose, including various contents (115, 230, 465 or 930 µg/lens) of a complex for detecting glucose, reacts with a constant concentration of glucose (0.6 mM).

Figure 23A:
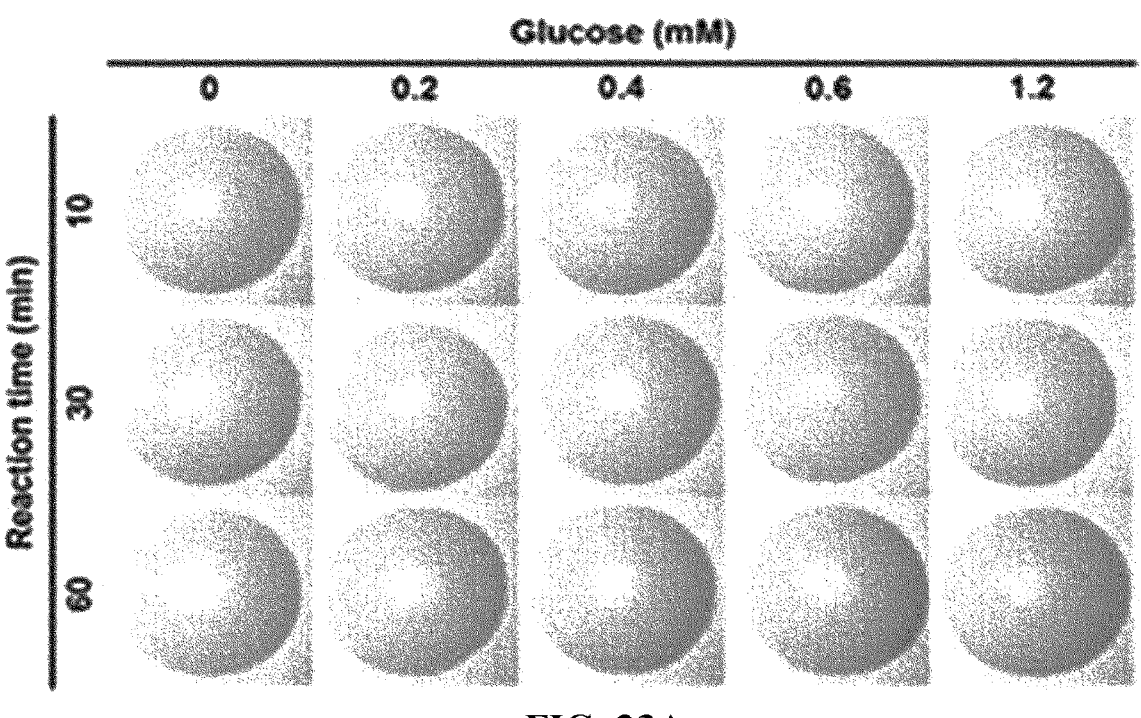

FIG. 23A shows a visual observation result of detecting a color change over time after a contact lens-type sensor for detecting glucose, including a complex for detecting glucose, reacts with various concentrations (0, 0.2, 0.4, 0.6, 0.8, 1 and 1.2 mM) of glucose in buffer.

Figure 23B:
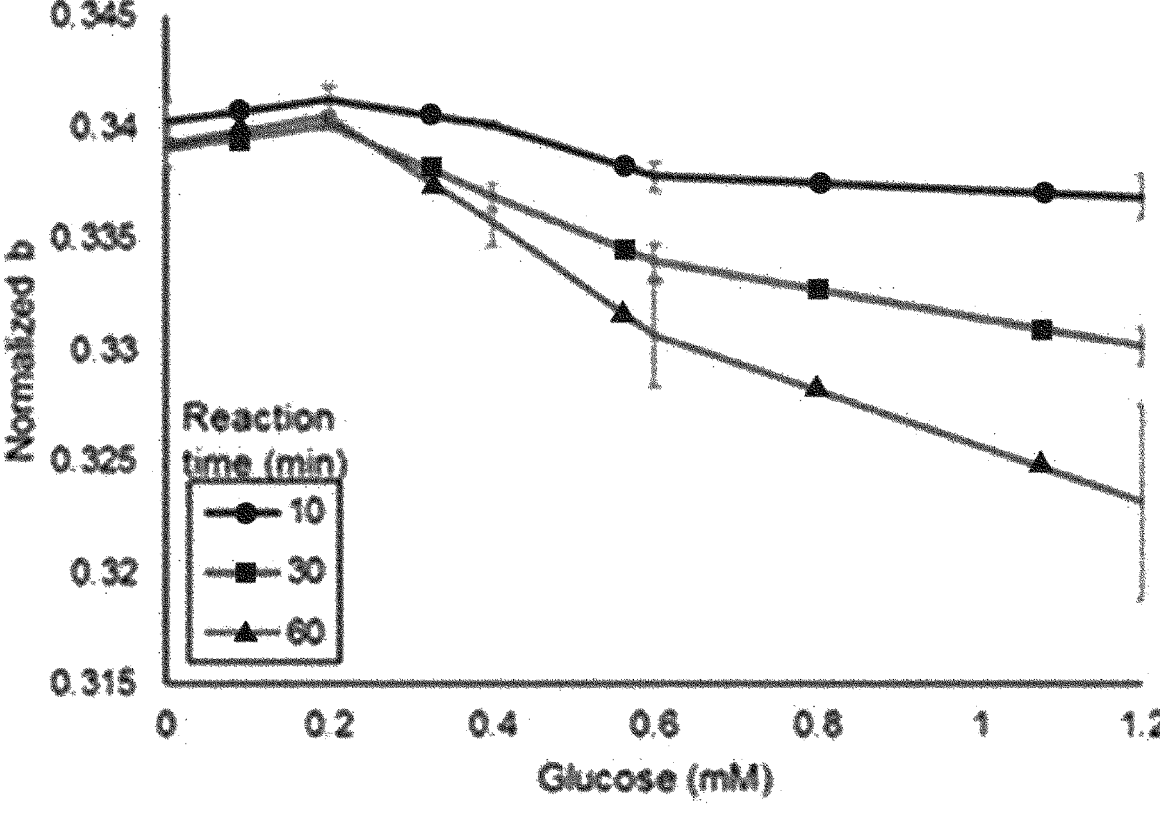

FIG. 23B shows a result of color intensity analysis (RGB values) over time after a contact lens-type sensor for detecting glucose, including a complex for detecting glucose, reacts with various concentrations (0, 0.2, 0.4, 0.6, 0.8, 1 and 1.2 mM) of glucose in buffer.

Figure 24A:
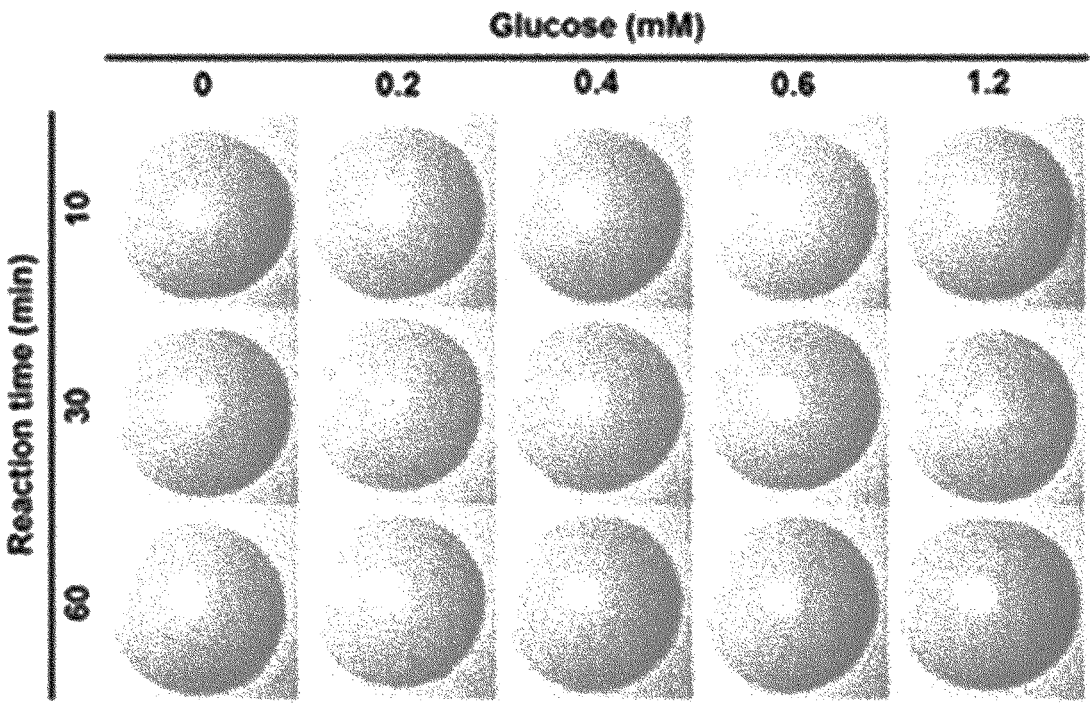

FIG. 24A shows a visual observation result of detecting a color change over time after a contact lens-type sensor for detecting glucose, including a complex for detecting glucose, reacts with various concentrations (0, 0.2, 0.4, 0.6, 0.8, 1 and 1.2 mM) of glucose in artificial tears.

Figure 24B:
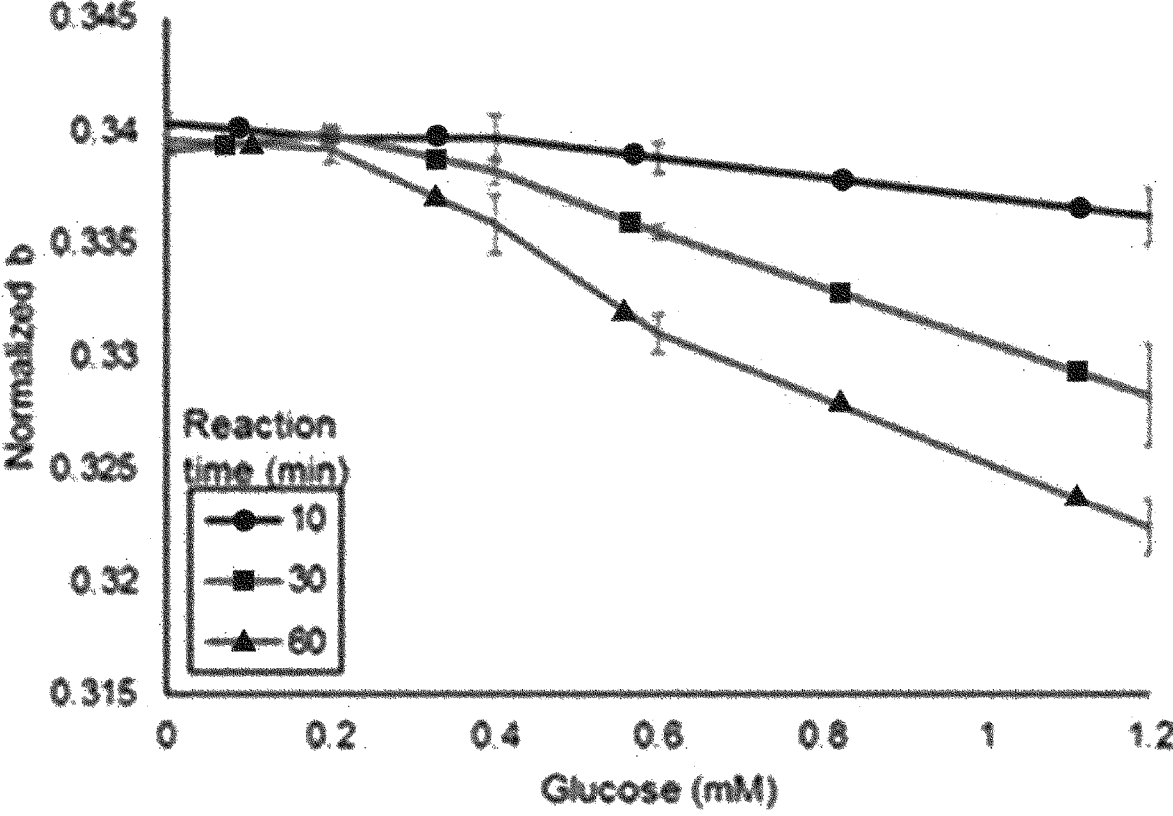

FIG. 24B shows a result of color intensity analysis (RGB values) over time after a contact lens-type sensor for detecting glucose, including a complex for detecting glucose, reacts with various concentrations (0, 0.2, 0.4, 0.6, 0.8, 1 and 1.2 mM) of glucose in artificial tears.

Figure 25:
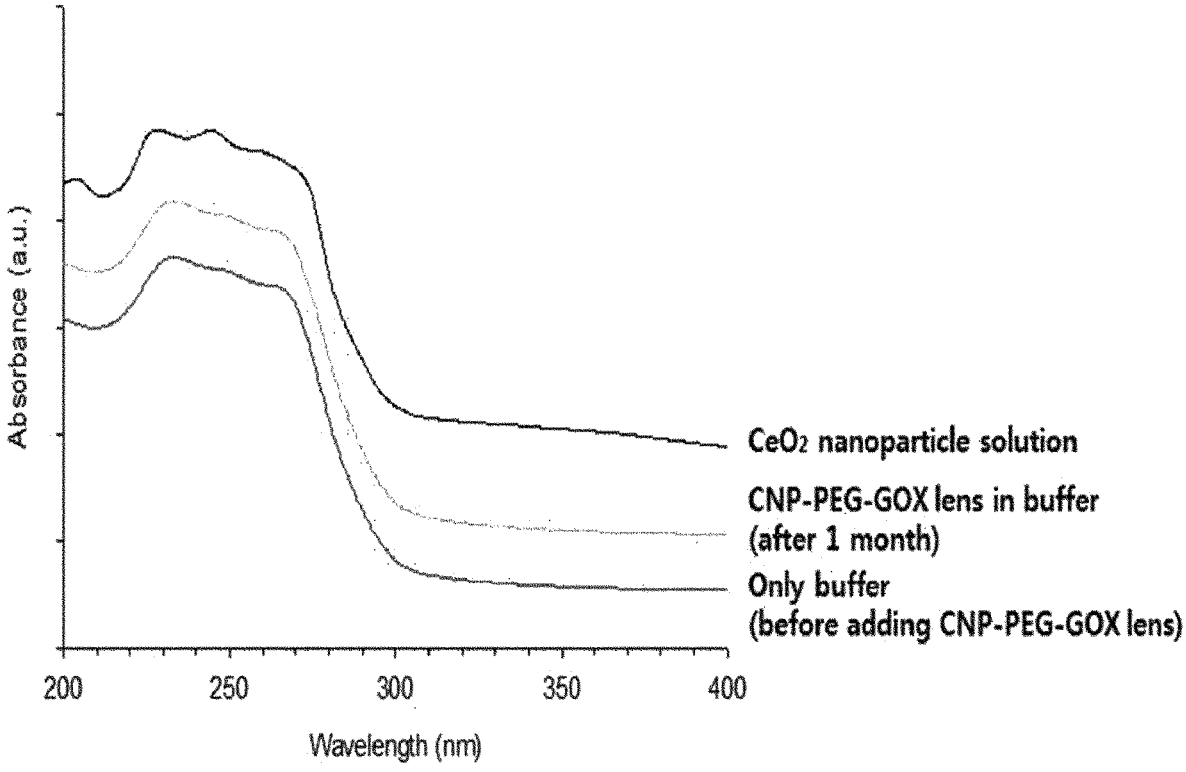

FIG. 25 shows a result of confirming cerium oxide nanoparticles in a solution using a UV-Vis spectrum after a contact lens-type sensor for detecting glucose according to the present invention is stored in a 0.9% NaCl solution for 1 month.

Figure 26A:
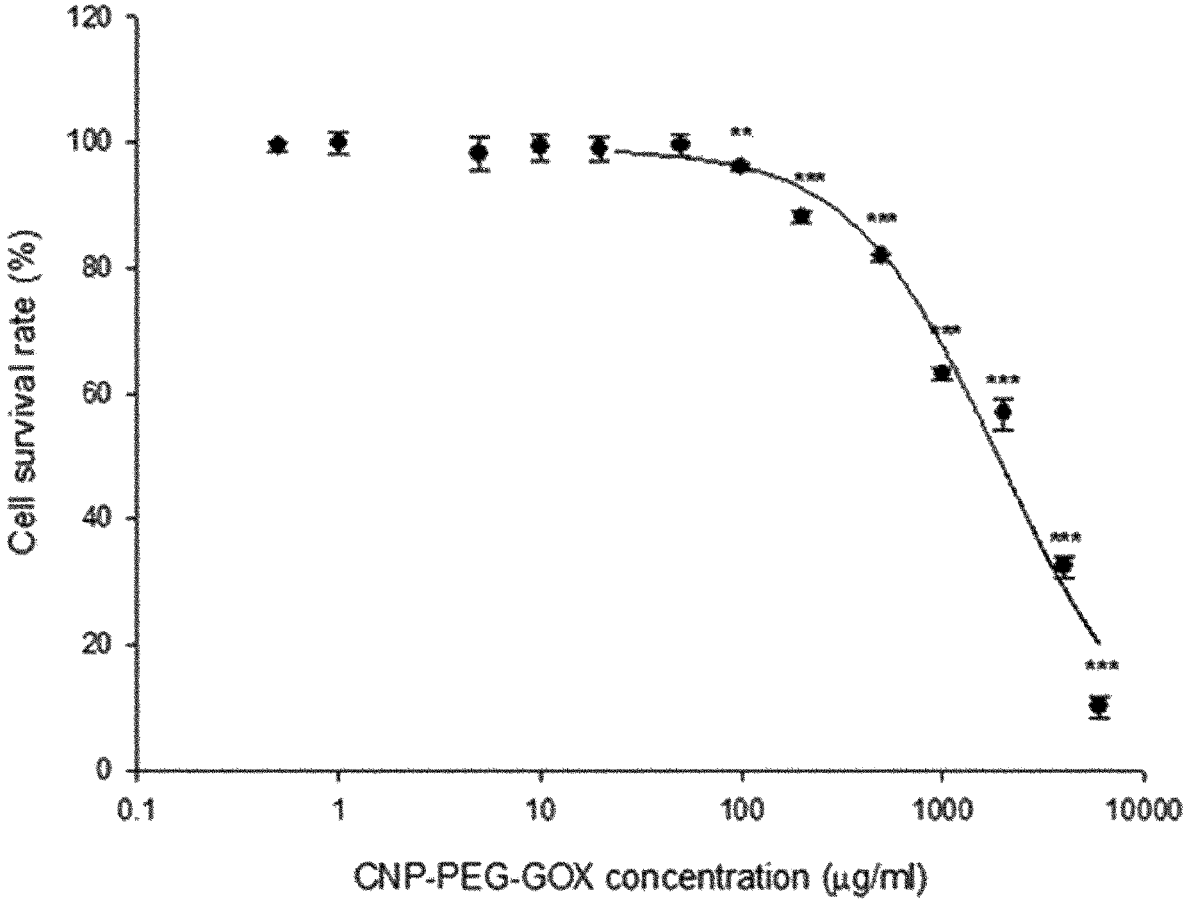

FIG. 26A shows a result of confirming a cell survival rate 24 hours after cells are treated with various concentrations (1 to 10000 µg/ml) of a complex for detecting glucose.

Figure 26B:
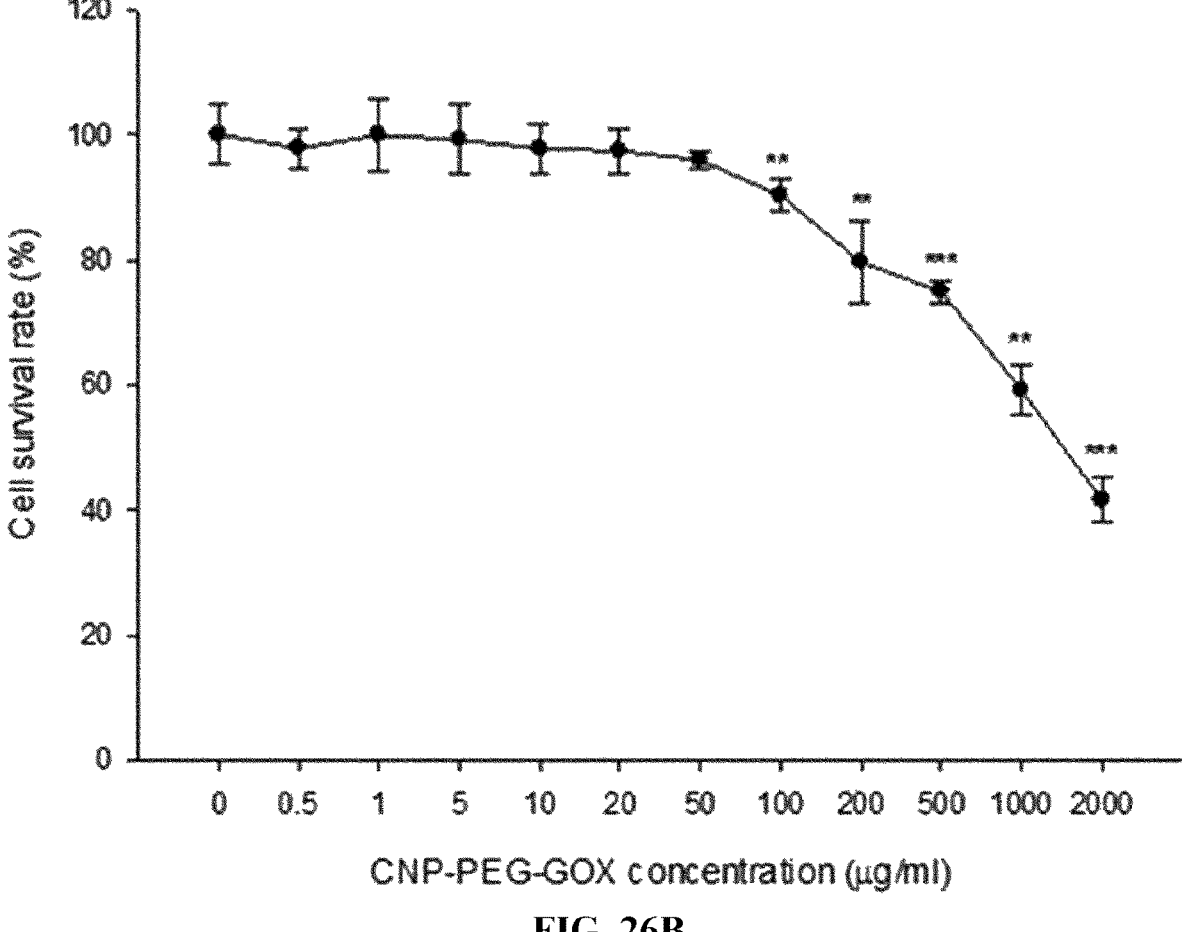

FIG. 26B shows a result of confirming a cell survival rate 48 hours after cells are treated with various concentrations (1 to 10000 µg/ml) of a complex for detecting glucose.

Figure 26C:
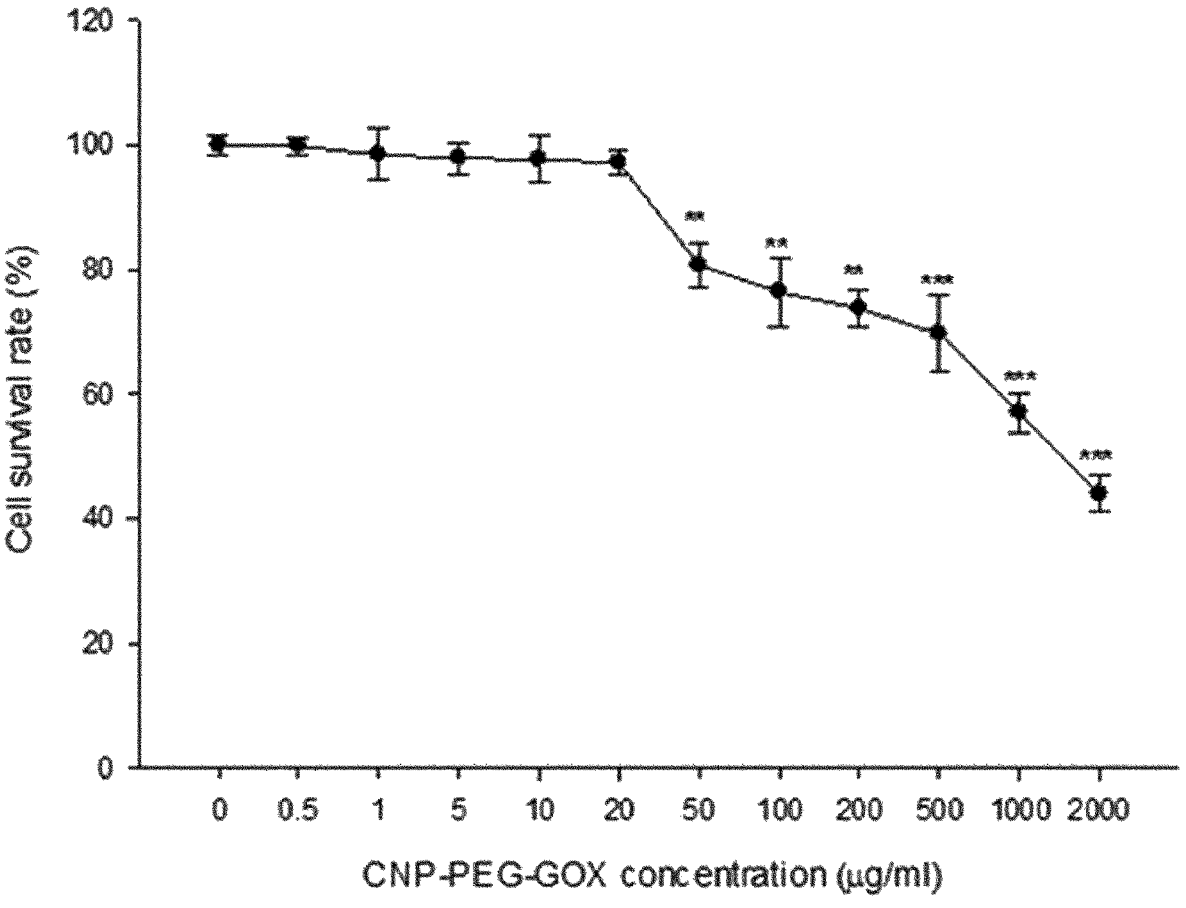

FIG. 26C shows a result of confirming a cell survival rate 72 hours after cells are treated with various concentrations (1 to 10000 µg/ml) of a complex for detecting glucose.

Figures 27A, 27B:
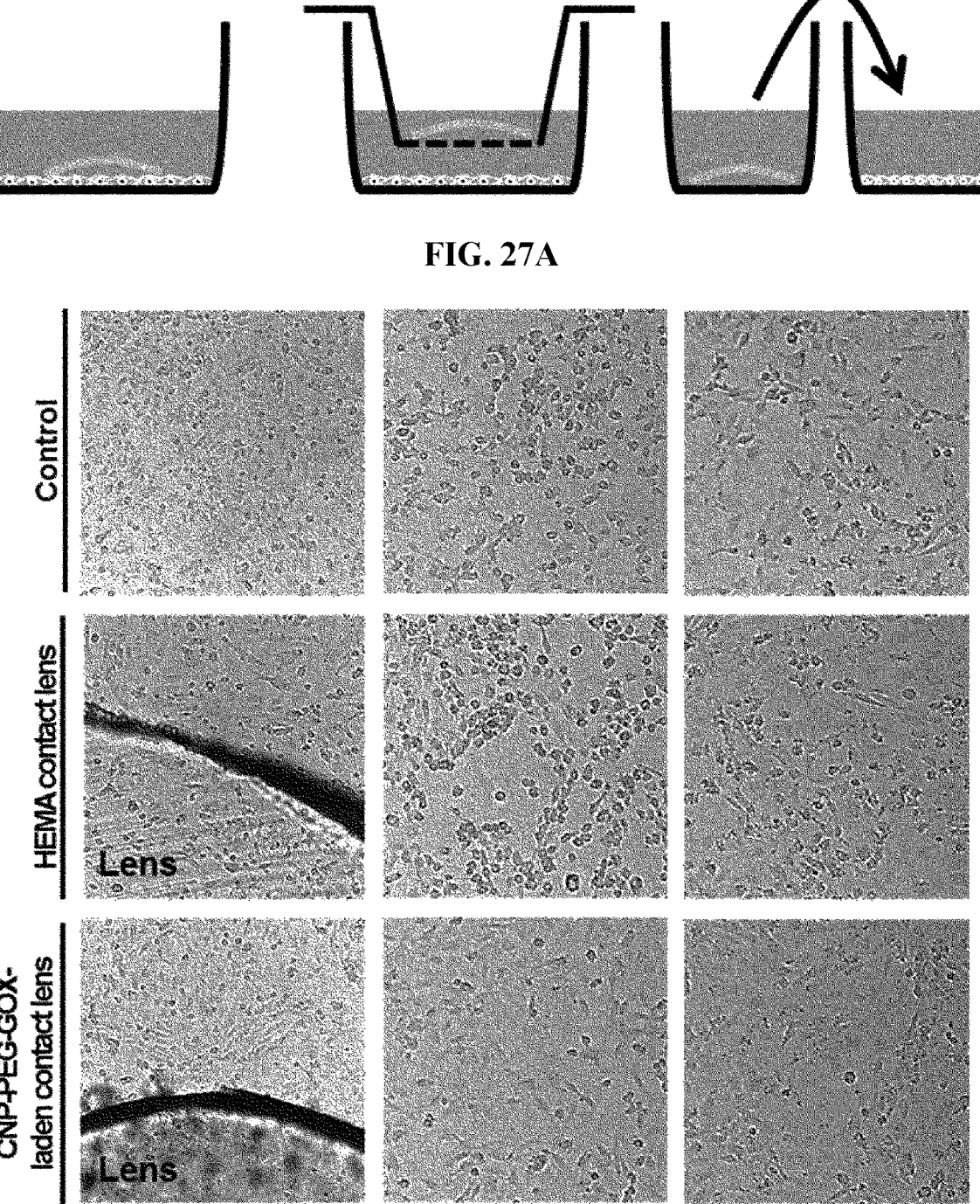

FIG. 27A is a schematic diagram illustrating a process of treating cells with a contact lens-type sensor in an exemplary embodiment to evaluate cytotoxicity of a contact lens-type sensor for detecting glucose according to the present invention.

FIG. 27B shows the distribution of cells according to the treatment as shown in FIG. 26A to evaluate cytotoxicity of a contact lens-type sensor for detecting glucose according to the present invention.

Figure 27C:
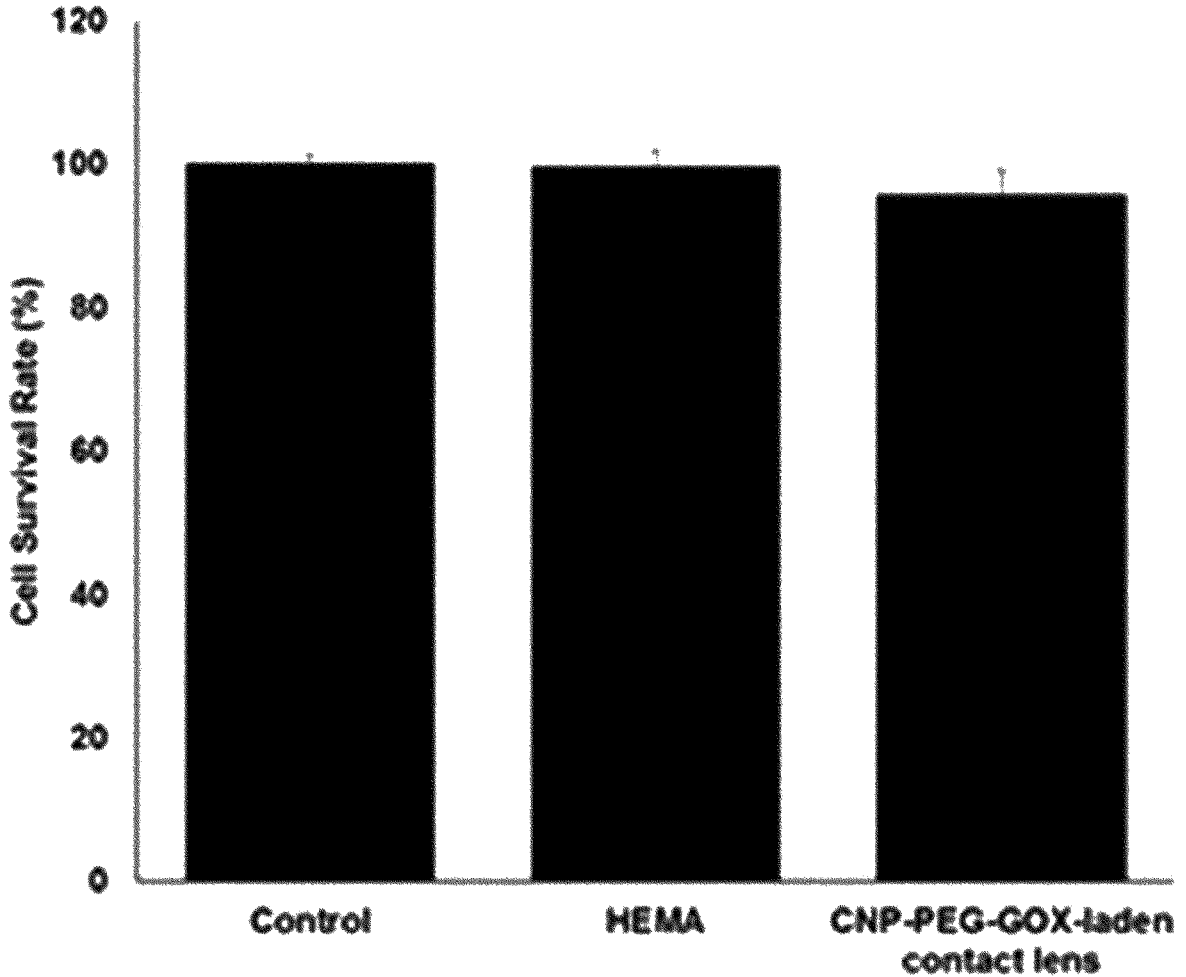

FIG. 27C shows the cell survival rate according to the treatment as shown in FIG. 26A to evaluate cytotoxicity of a contact lens-type sensor for detecting glucose according to the present invention.

Figure 28A:
Figure 28A:
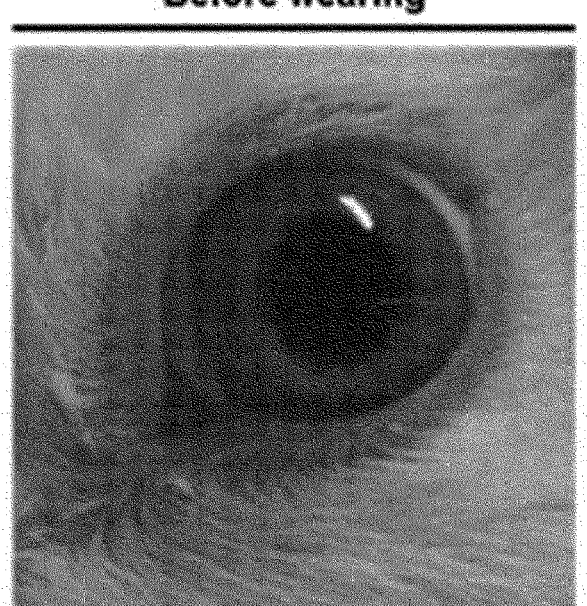
Figure 28A:
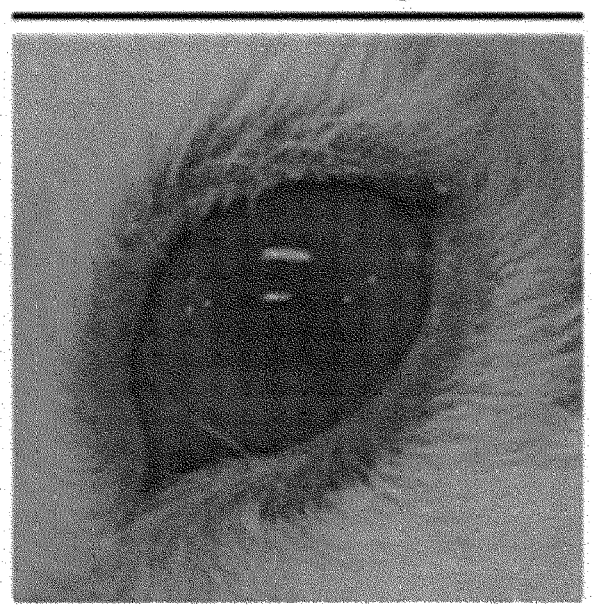

FIG. 28A shows a visual observation result of detecting a colorimetric reaction of a contact lens-type sensor for detecting glucose according to the present invention for an animal model in which high blood sugar is temporarily induced.

Figure 28B:
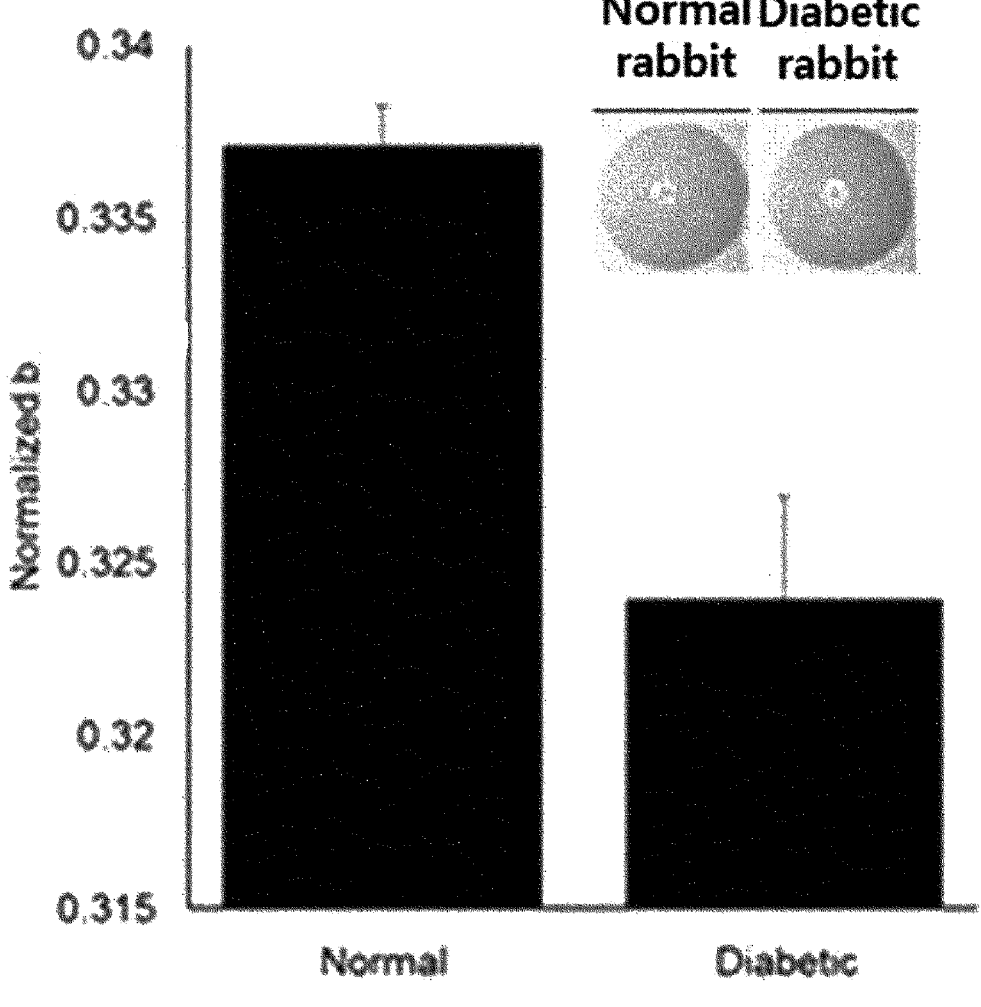

FIG. 28B shows a color intensity analysis (RGB values) result for detecting a colorimetric reaction of a contact lens-type sensor for detecting glucose according to the present invention for an animal model in which high blood pressure is temporarily induced.

Figure 29A:
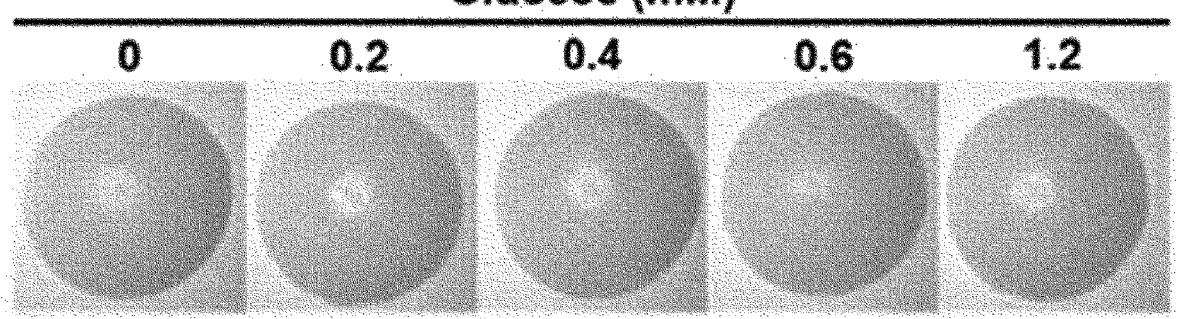

FIG. 29A shows a visual observation result of detecting a colorimetric reaction of a contact lens-type sensor for detecting glucose according to the present invention according to a change in glucose concentration in tears for an animal model in which high blood pressure is temporarily induced.

Figure 29B:
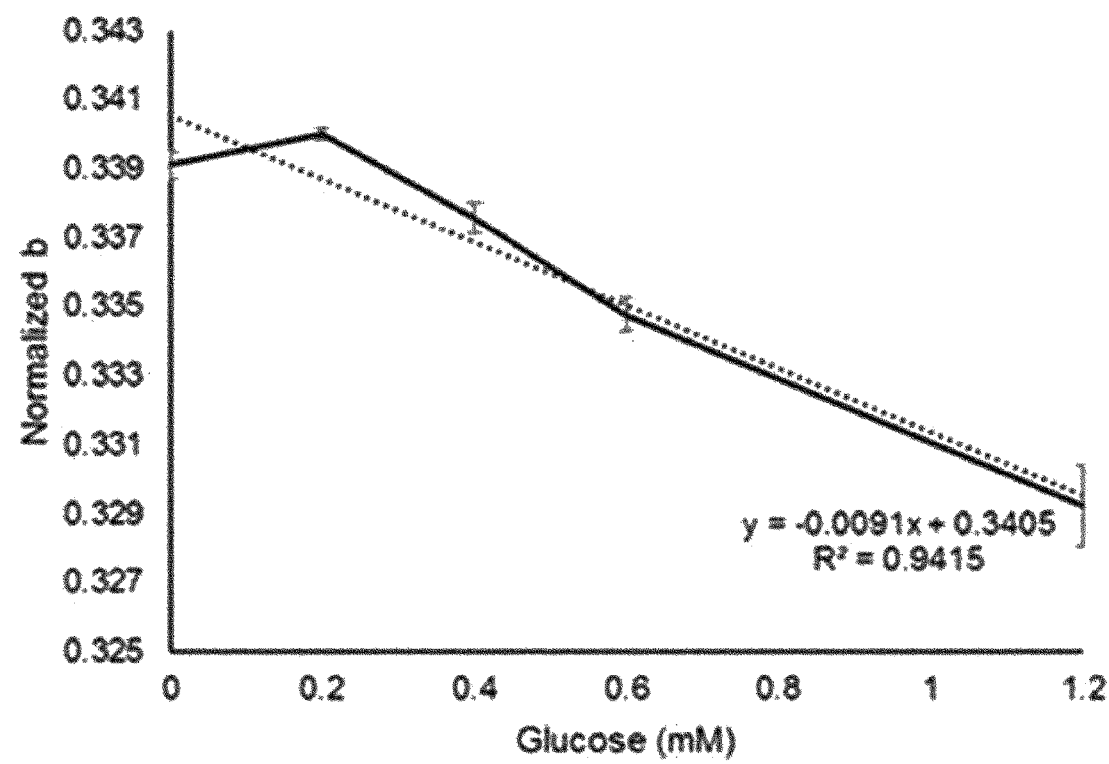

FIG. 29B is a result of analyzing a glucose concentration in tears through a measured color intensity for an animal model in which high blood pressure is temporarily induced.

Figure 30A:
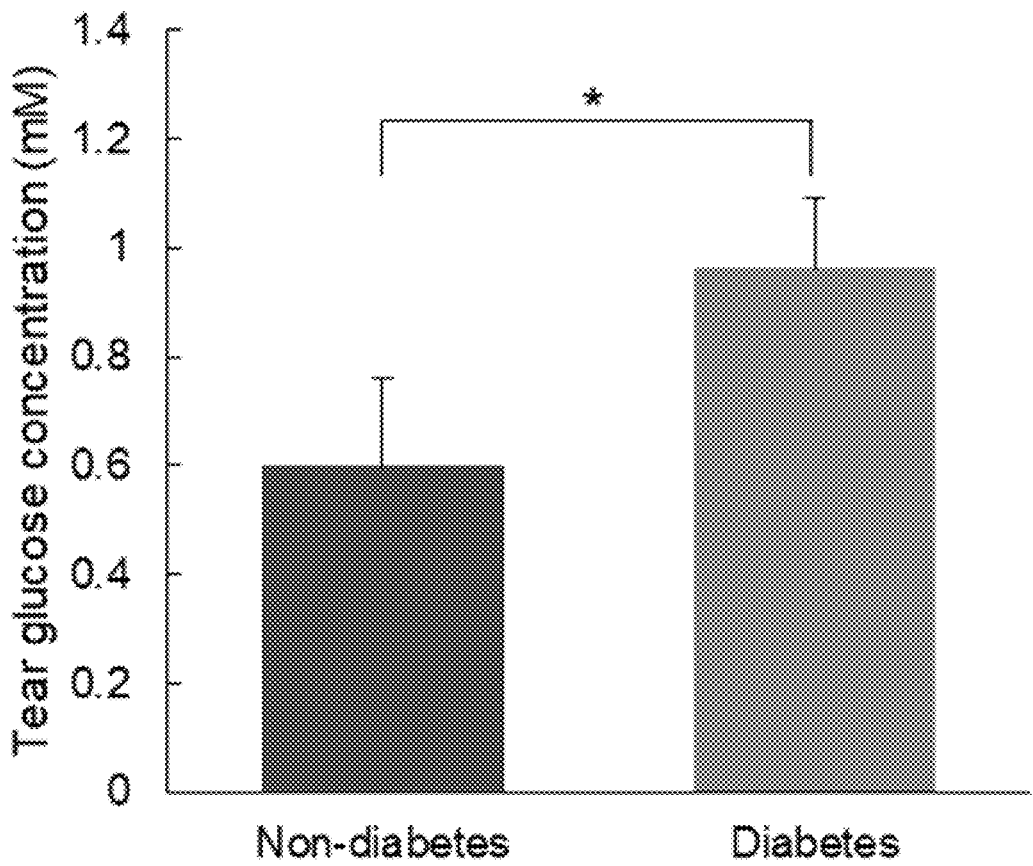

FIG. 30A shows a result of analyzing a glucose concentration in tears using the CNP-PEG-GOx-laden contact lenses for an animal model in which high blood pressure is temporarily induced.

Figure 30B:
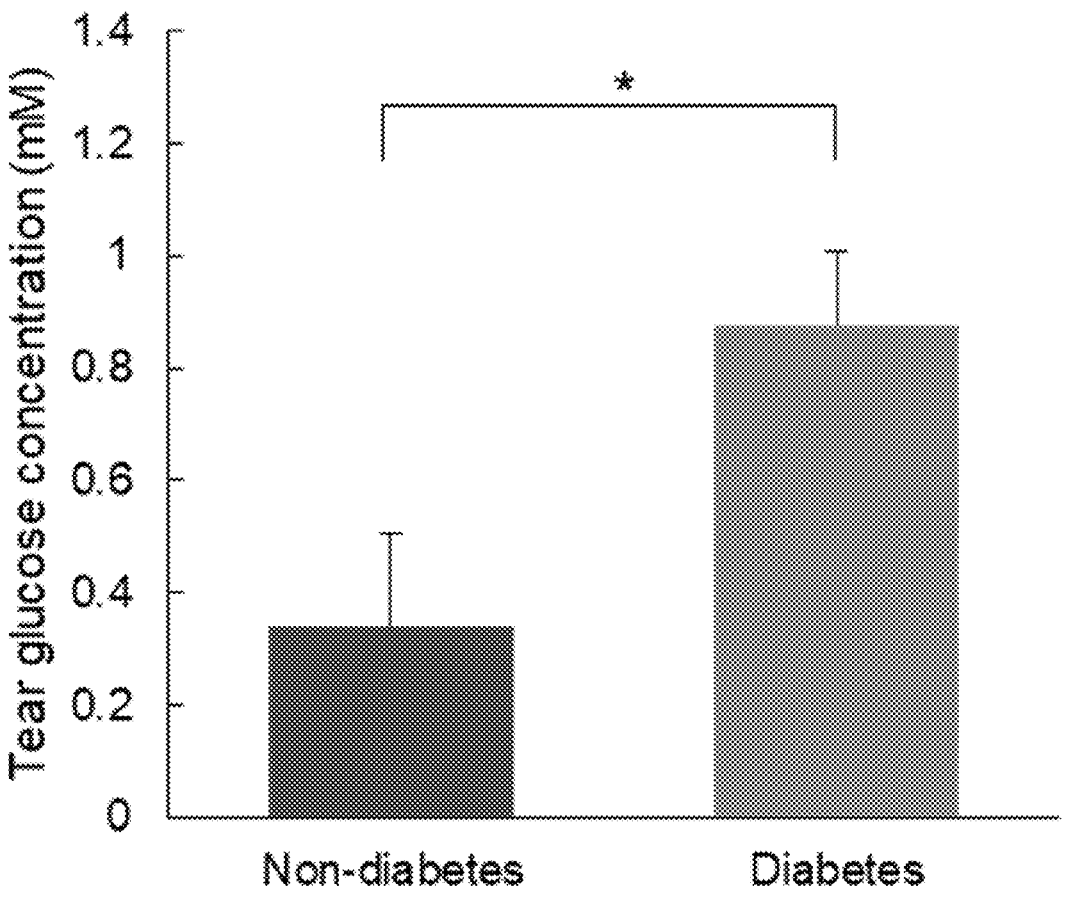

FIG. 30B shows a result of analyzing a glucose concentration in tears using a glucose assay kit for an animal model in which high blood pressure is temporarily induced.

Figure 30C:
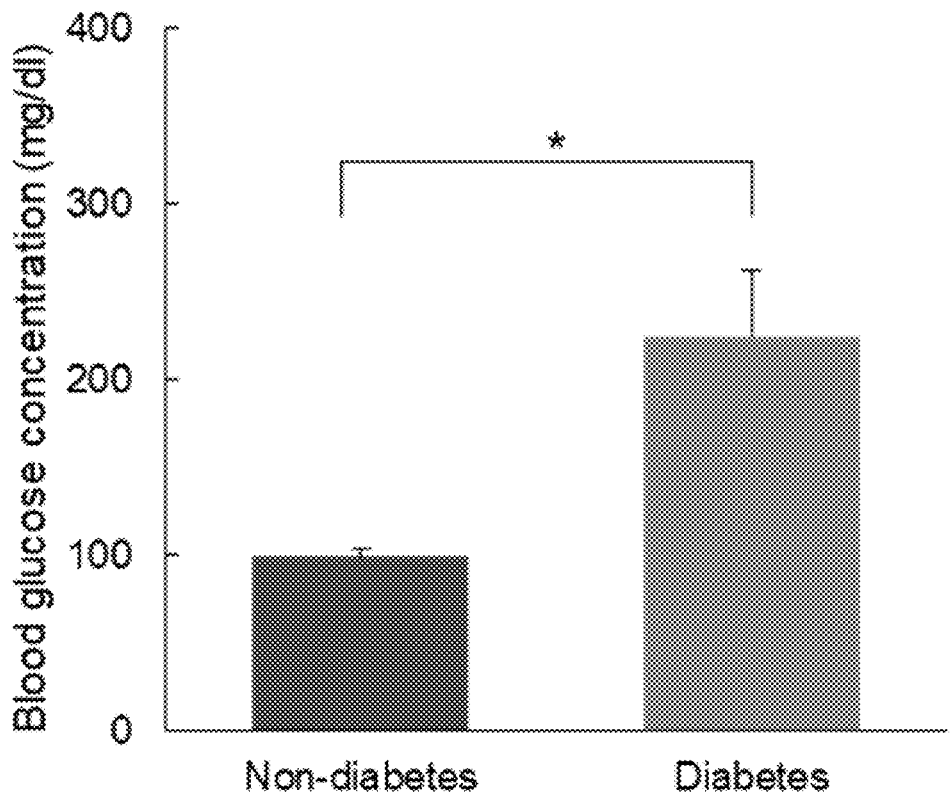

FIG. 30C shows a result of analyzing a glucose concentration in tears using a finger-prick test with a portable blood glucometerfor an animal model in which high blood pressure is temporarily induced.

MODES OF THE INVENTION

Hereinafter, the present invention will be described in detail.

The present invention provides a contact lens-type sensor for detecting glucose, which includes a complex for detecting glucose, which includes cerium oxide nanoparticles and glucose oxidase.

The glucose oxidase, used herein, is a material for recognizing glucose in the body, and serves to produce hydrogen peroxide ($H_2O_2$) by a reaction with glucose, and the produced hydrogen peroxide induces a colorimetric reaction of cerium oxide.

The cerium oxide nanoparticles used in the present invention is a material for visualizing detected glucose or a concentration thereof, and cerium constituting the nanoparticle is a rare earth element in the lanthanide series. Due to a characteristic of converting oxidation states between 3 and 4, reversible oxidation/reduction is possible. Particularly, in the reaction of the cerium oxide nanoparticle with hydrogen peroxide, $Ce^{3+}$ being colorless reacts with a hydroxyl radical produced from hydrogen peroxide and is oxidized to $Ce^{4+}$, which is yellow. Through the complex of the present invention, hydrogen peroxide is produced by the reaction between glucose in the body and glucose oxidase, and the produced hydrogen peroxide may induce a color change in the cerium oxide nanoparticles. Through the colorimetric reaction, glucose may be detected.

To detect glucose as described above, the cerium oxide nanoparticles may be included at a concentration of 0.1 to 0.6 w/v % with respect to the total volume of the complex. When the concentration of the cerium oxide nanoparticles is extremely low, it may be difficult to detect the colorimetric reaction, and when the concentration of the cerium oxide nanoparticles is extremely high, a problem in that it is impossible to tell a difference in the colorimetric reaction according to glucose concentration may be caused. Particularly, when the complex of the present invention is implemented in a contact lens-type sensor, considering that a tear glucose level should be measured by the difference in colorimetric reaction within the range (0.5 to 1.0 mM) of a tear glucose level, which can be clinically applied, the concentration of the cerium oxide nanoparticles is one of the key technical factors.

In the present invention, the cerium oxide nanoparticle and glucose oxidase may be linked by the interaction with a biocompatible polymer, and the biocompatible polymer is preferably a bio-affinitive monomer or polymer (n=1 to 30), and more preferably, polyethylene glycol, poly(acrylamide), poly(allylamine), poly(ethyleneimine), poly(amidoamine), polylysine, poly(lactide), poly(acrylic acid), poly(N-isopropylacrylamide), poly(2-(dimethyl-amino)ethyl methacrylate, poly(caprolactone), chitosan, poly(N-vinyl caprolactam), dextran, poly(styrene sulfate) or poly(vinyl sulfonic acid), and most preferably, polyethylene glycol. As long as a polymer includes a hydroxyl, carboxyl or amine group as a functional group of a terminal end, any polymer can be included without limitation, and if needed, a homofunctional or heterofunctional polymer may be applied. In addition, the cerium oxide nanoparticle, the biocompatible polymer and glucose oxidase may be sequentially conjugated, and the conjugation is preferably accomplished by a covalent bond, and more preferably an amide bond (peptide bond). Any bond capable of forming a single complex may be included without limitation.

The conventional method for invasively detecting blood glucose can make a scar in the skin, as well as causing stress and pain in a patient, and has an external infection possibility through blood, and thus the conventional method was somewhat problematic for application to diabetic patients who should be subjected to repeated detection of glucose, and as another method for non-invasively detecting blood glucose, there is a method for detecting glucose using sweat or saliva, but this method had a disadvantage of a wide error range such that exact detection is difficult. Therefore, in the present invention, based on the fact that there is a close relationship between a tear glucose level and a blood glucose level, a contact lens-type sensor including a complex capable of detecting glucose in tears was produced.

The contact lens-type sensor according to the present invention may be configured to include a main body of the contact lens (base); and a complex for detecting glucose present in the main body of the contact lens.

As the contact lens-type sensor according to the present invention should include the complex for detecting glucose at a suitable concentration for having a physical property (e.g., elastic modulus) which can be directly applied to an eyeball, the complex for detecting glucose in the contact lens-type sensor may be included in the range of 115 to 930 μg, and more specifically, 0.3 to 2.5 wt % (w/v) with respect to the total volume of the contact lens-type sensor, based on a lens generally known in the art, but the present invention is not limited thereto. When the concentration of the complex for detecting glucose is excessively low, a colorimetric reaction for detecting glucose may be weak, and when the concentration of the complex for detecting glucose is excessively high, since the contact lens-type sensor itself is yellow, the intrinsic function of the lens may be negatively influenced, and measurement of a glucose concentration may also be influenced by the measurement in color intensity.

Meanwhile, contact lens-type sensors that are currently under research include a form including an electrode for current measurement and a form including a substance exhibiting fluorescence by the reaction with glucose. However, these sensors have a disadvantage in that they need an additional measurement apparatus for detecting glucose. Particularly, the former had a possibility of damaging an eyeball due to heat generated from a circuit since it includes various types of ultra-small control circuits, communication circuits and antennae, any one of which is inserted into a contact lens, and the latter had a possibility of damaging an eyeball since an external light source should be directly applied to the eyeball to detect glucose. Therefore, the contact lens-type sensor according to the present invention includes a complex consisting of glucose oxidase which can specifically react with glucose; and cerium oxide nanoparticles which is colored by the hydrogen peroxide produced by the reaction, and thus is used to more simply detect glucose in tears.

In addition, the complex in the contact lens-type sensor was manufactured and disposed in the form of being entrapped in the biocompatible polymer, thereby minimizing a side effect which can affect an eyeball and improving glucose detection efficiency. Specifically, methods for loading a synthesized complex in a contact lens are broadly classified into three types: 1) entrapment; 2) chemical conjugation with a surface functional group of the contact lens; and 3) loading into a carrier such as a liposome to put in a contact lens. Most of all, when the surface functional group of the contact lens-type sensor is directly conjugated with the complex, as the conjugation is performed on the surface (plane), a great amount of the complex in the sensor may not be contained due to a spatial limit, and there is a possibility of causing cytotoxicity. In addition, when a carrier is used, to react with the complex in the contact lens-type sensor, since a substrate, glucose, should pass through a polymer and a carrier layer, which constitute a contact lens, there was a possibility of reducing reactivity. However, as the preset invention uses entrapment among these methods, a change in the activity of the nanoparticle caused by modification of the complex, which is caused in a loading process, and particularly, the modification of a functional group, may be minimized, the complex may be contained in an amount as much as the thickness and volume of a lens allow, thereby not only enhancing glucose detection efficiency, but also the mixing thereof in a contact lens-type sensor. Therefore, as long as the complex is not released again from the sensor, there is almost no possibility of cytotoxicity.

In addition, according to an experiment, it was able to be seen that the contact lens-type sensor according to the present invention shows a significant colorimetric reaction under a glucose condition of a concentration range of approximately 0.2 to 2 mM including the concentration (0.5 to 1.0 mM) of glucose in tears of a diabetic patient, and such a colorimetric reaction is linearly proportional to the glucose concentration. Therefore, there is an advantage in that it is possible to quantitatively detect a glucose concentration using colorimetric analysis (e.g., RGB color intensity analysis) known in the art (refer to Example 9).

A monomer of the biocompatible polymer may be 2-hydroxyethyl methacrylate, N-vinyl pyrrolidone, methacrylate, methyl methacrylate or vinyl pyrrolidone, but any monomer capable of being applied to the production of a conventional contact lens can be included without limitation.

According to an exemplary embodiment of the present invention, it can be confirmed that a complex for detecting glucose may be prepared by sequentially conjugating polyethylene glycol and glucose oxidase to cerium oxide nanoparticles, and the complex for detecting glucose is colored according to a glucose concentration, confirming that such color intensity is linearly proportional to a glucose concentration (see Preparation Example 1 and Example 3).

According to another exemplary embodiment of the present invention, based on the complex for detecting glucose, a contact lens-type sensor capable of detecting glucose in tears may be produced, a glucose concentration may be quantitatively measured by the colorimetric reaction of cerium oxide as described above, confirming that the contact lens which can be directly applied to an eyeball is excellent in terms of physical properties, storage stability and cytotoxicity (see Preparation Example 2, and Examples 4 to 9).

The present invention also provides a method for detecting glucose, which includes a composition for detecting glucose which includes the nanoparticle complex; a use of the complex for detecting glucose; and administering the complex to a subject.

The present invention also provides a use of the contact lens-type sensor for detecting glucose; and a method for detecting glucose, which includes administering the contact lens-type sensor to a subject or treating a subject therewith.

The present invention may further include performing color intensity analysis for the contact lens-type sensor according to the above-mentioned treatment. According to an exemplary embodiment of the present invention, it can be seen that the colorimetric reaction of a complex for detecting glucose and a contact lens-type sensor is linearly proportional to a glucose concentration. Therefore, in the above step, based on this correlation, the tear glucose level may be specifically quantified, ultimately deducing a blood glucose level.

In the present invention, the step of administering to a subject or treating a subject may be performed by wearing the contact lens on an eyeball of the subject.

The term "subject" used herein refers to a subject in need of glucose detection for detecting and monitoring a disease such as diabetes, and more specifically, a mammal such as a human, or a non-human primate, a mouse, a rat, a dog, a cat, a horse, or a cow.

In still another aspect, the present invention provides a method for producing a contact lens-type sensor for detecting glucose, which includes: (a) adding a complex for detecting glucose of the present invention to a mixed solution including a monomer of a biocompatible polymer, a crosslinking agent, etc.; and (b) adding the complex-added mixed solution to a mold in the form of a contact lens to perform crosslinking.

Hereinafter, to help in understanding the present invention, exemplary examples will be suggested. However, the following examples are merely provided to more easily understand the present invention, and not to limit the present invention.

PREPARATION EXAMPLES

Preparation Example 1. Preparation of Cerium Oxide-Derived Complex for Detecting Glucose First, $Ce(NO_3)_36H_2O$ (1.736 g), NaOH (400 mg) and distilled water (128 ml) were mixed in a stirrer for 48 hours at room temperature, and impurities were removed with distilled water, thereby obtaining cerium oxide nanoparticles ($CeO_2$ nanoparticles; CNPs). Subsequently, the CNPs (250 mg) were dissolved in NaOH (1M), epichlorohydrin and NaOH (2M) were added thereto, the mixture was stirred for 8 hours and then washed, 30% $NH_4OH$ was further added thereto, and the resulting mixture was stirred for 14 hours and washed, followed by introduction of an amine group to the CNPs ($CeO_2$—$NH_2$; m.w. 150 kDa). Afterward, the amine group-introduced CNPs and bifunctional PEG (NHS-PEG-COOH; m.w. 2 kDa) were added to a buffer at a molar ratio of 1:4, and the mixture was stirred for 60 minutes and washed, followed by introduction of PEG ($CeO_2$-PEG-COOH). Finally, EDC (2 mM) and NHS (5 mM) were added to MES buffer (pH 6) so that PEG-introduced CNPs were dissolved at a concentration of 1 mg/ml and stirred for 20 minutes at room temperature. Afterward, the pH was adjusted to 7.4, glucose oxidase (GOx) was added to the resulting mixture, the mixture was stirred for 1 hour, and impurities were removed with distilled water, thereby preparing a cerium oxide-based complex for detecting glucose to which glucose oxidase is conjugated (in the following examples, the cerium oxide-based complex for detecting glucose will be named a complex for detecting glucose or a $CeO_2$-PEG-GOx complex).

Preparation Example 2. Production of Contact
Lens-Type Sensor for Detecting Glucose in Tears Methacrylic acid (MAA, 34 µl) and ethylene glycol dimethacrylate (EGDMA; 105 µl) were dissolved in hydroxyethyl methacrylate (HEMA; 4 ml), and Darocure (17 µl) as a photoinitiator was added. Afterward, the complex for detecting glucose ($CeO_2$-PEG-GOx) of Preparation Example 1 was added, and sonification was performed to disperse a mixed solution. The solution was injected into a mold for forming a contact lens shape, UV polymerization (365 nm, 15 mW/cm$^2$) was performed for 30 minutes, and distilled water and NaCl (0.9%) were used for washing every two days, thereby producing a contact lens-type sensor according to the present invention for detecting glucose in tears (in the following examples, the sensor will named a contact lens-type sensor for detecting glucose or a contact lens-type sensor). The produced contact lens-type sensor was stored in NaCl (0.9%) in a refrigerator before use.

EXAMPLES

Example 1. Confirmation of Product in Process of
Preparing Complex for Detecting Glucose The process of preparing the complex for detecting glucose of Preparation Example 1 broadly includes 1) introduction of an amine group to CNPs ($CeO_2$—$NH_2$), 2) introduction of PEG to the nanoparticle ($CeO_2$-PEG-COOH), and 3) conjugation of glucose oxidase to the PEG ($CeO_2$-PEG-GOx), and in this example, each product produced in this process was to be confirmed. Specifically, in the process of substituting a hydroxyl group on a CNP surface with an amine group, peak shifting was examined to confirm synthesis of amine group-introduced CNPs, ATR-FTIR spectroscopy was performed to confirm the conjugation between CNPs and PEG, and BCA assay was performed to confirm an amount of glucose oxidase, and therefore the conjugation between PEG and glucose oxidase was confirmed for each product. In addition, a purity of the complex for detecting glucose was evaluated by comparing the synthesis of the complex for detecting glucose of Preparation Example 1 and an SDS-PAGE result for the complex (lane 3) with a case in which only glucose oxidase (lanes 1 and 2) was loaded or a case in which both a glucose oxidase and a nano complex were loaded (lane 3).

Figure 1A:
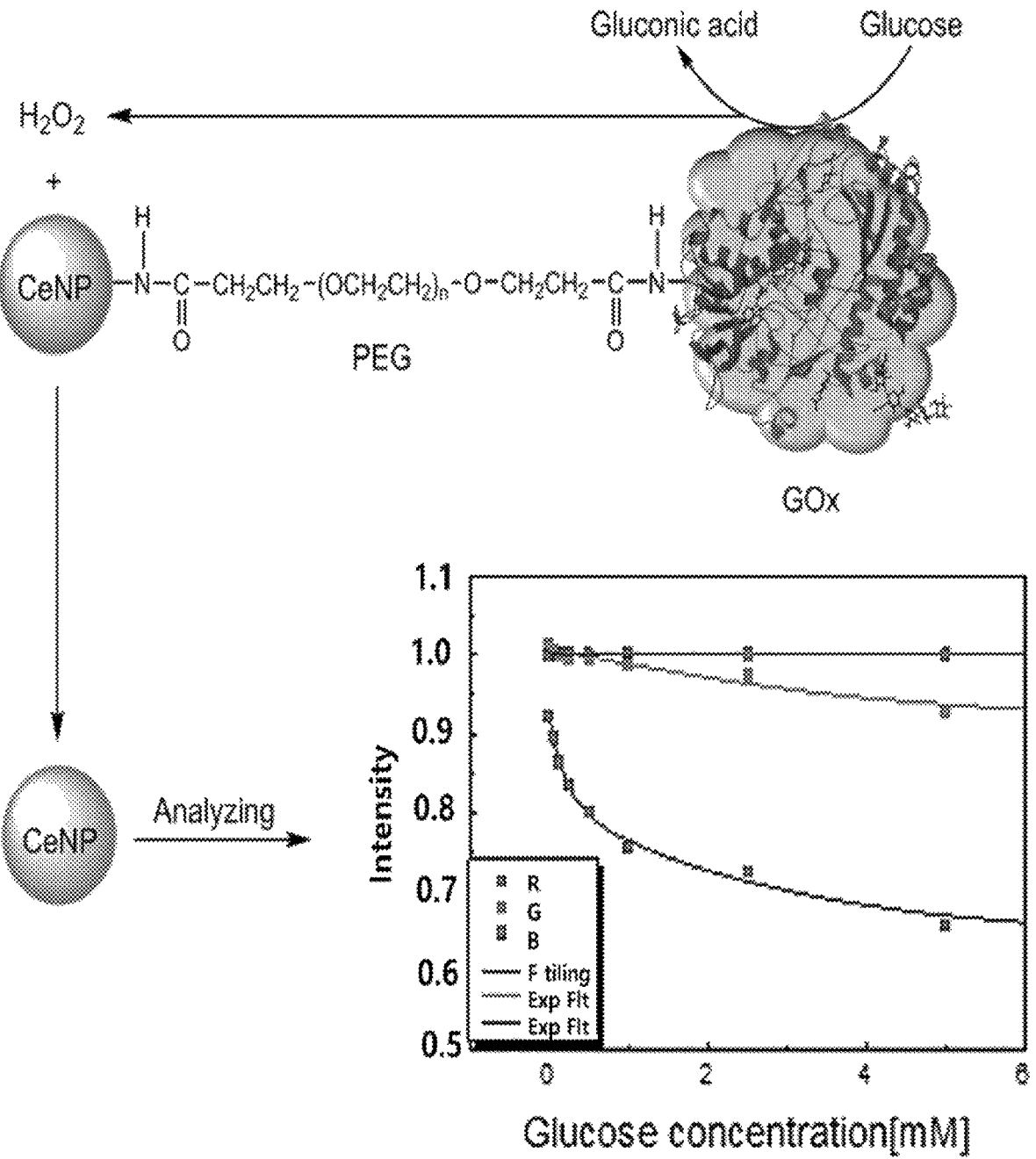
FIG. 1A illustrates a process of detecting a glucose concentration using a complex for detecting glucose.
Figure 1B:
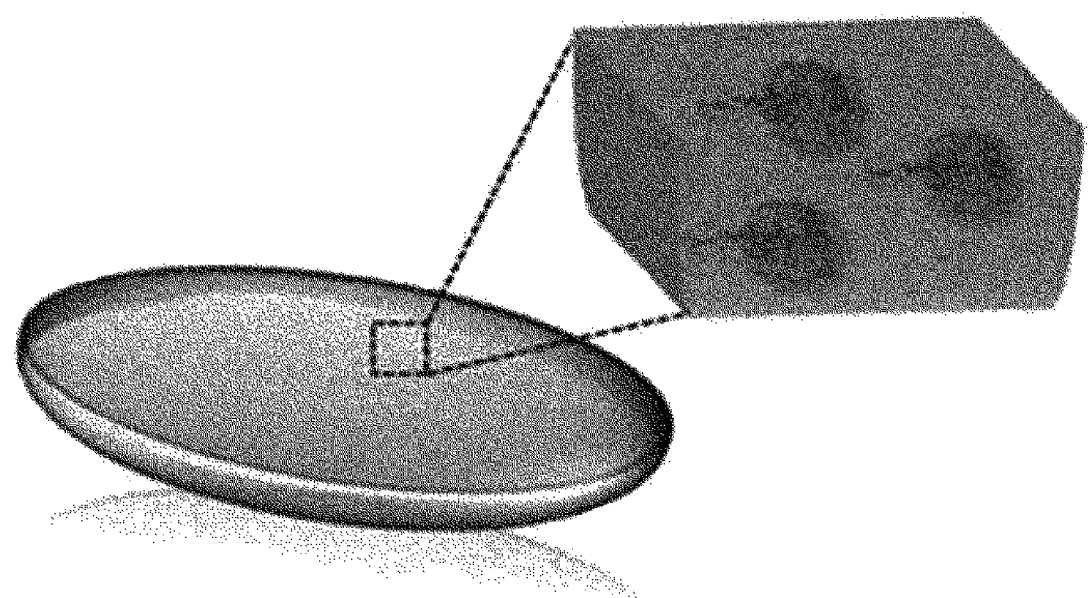
FIG. 1B illustrates the configuration of a contact lens-type sensor for detecting glucose according to an exemplary embodiment of the present invention.
Figure 2A:
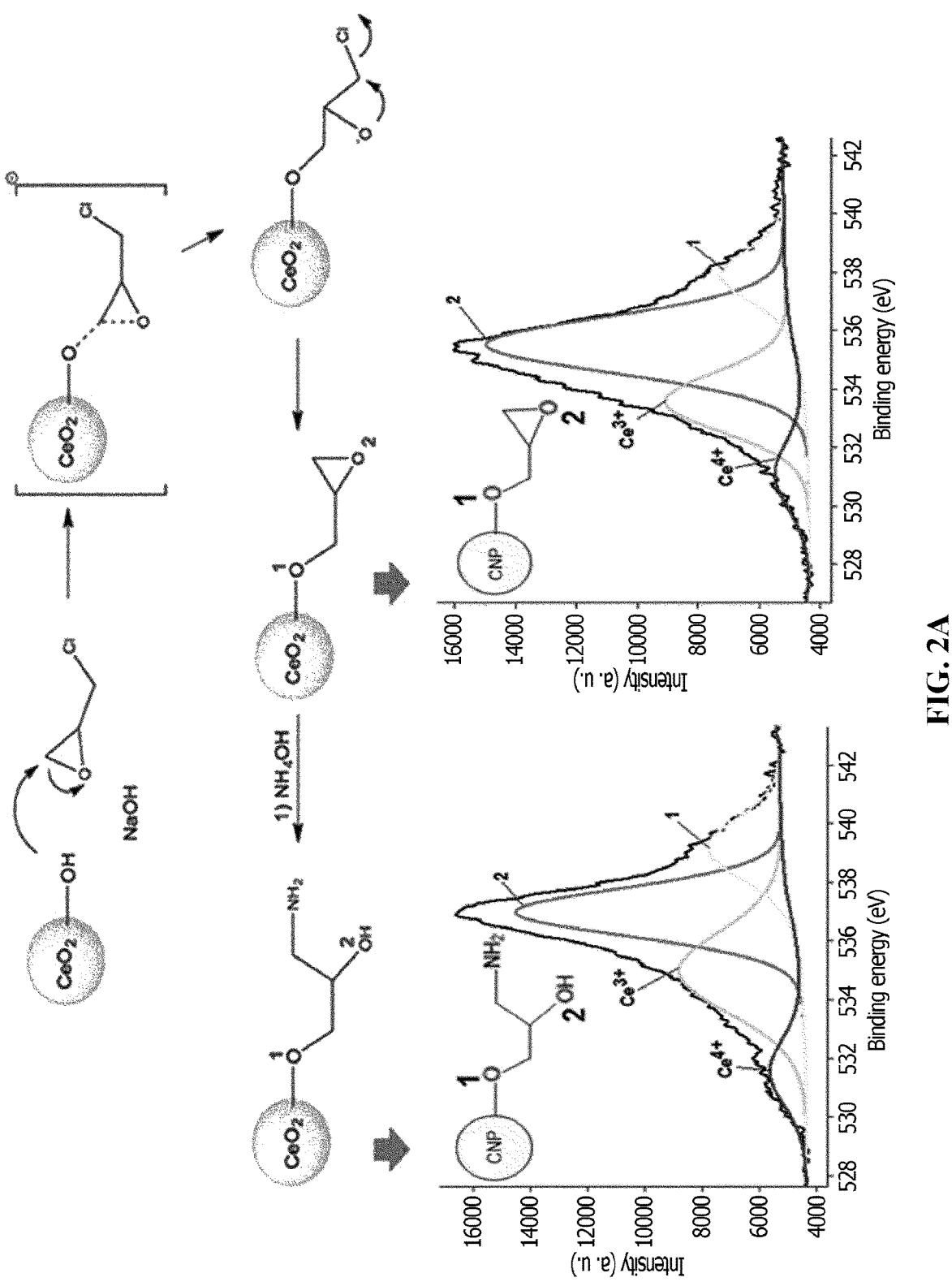
FIG. 2A schematically illustrates a process of introducing an amine group to cerium oxide nanoparticles ($CeO_2$—$NH_2$) according to the present invention, and shows an XPS result confirming peak shifting in a process of substituting a hydroxyl group with an amine group.
Figure 2B:
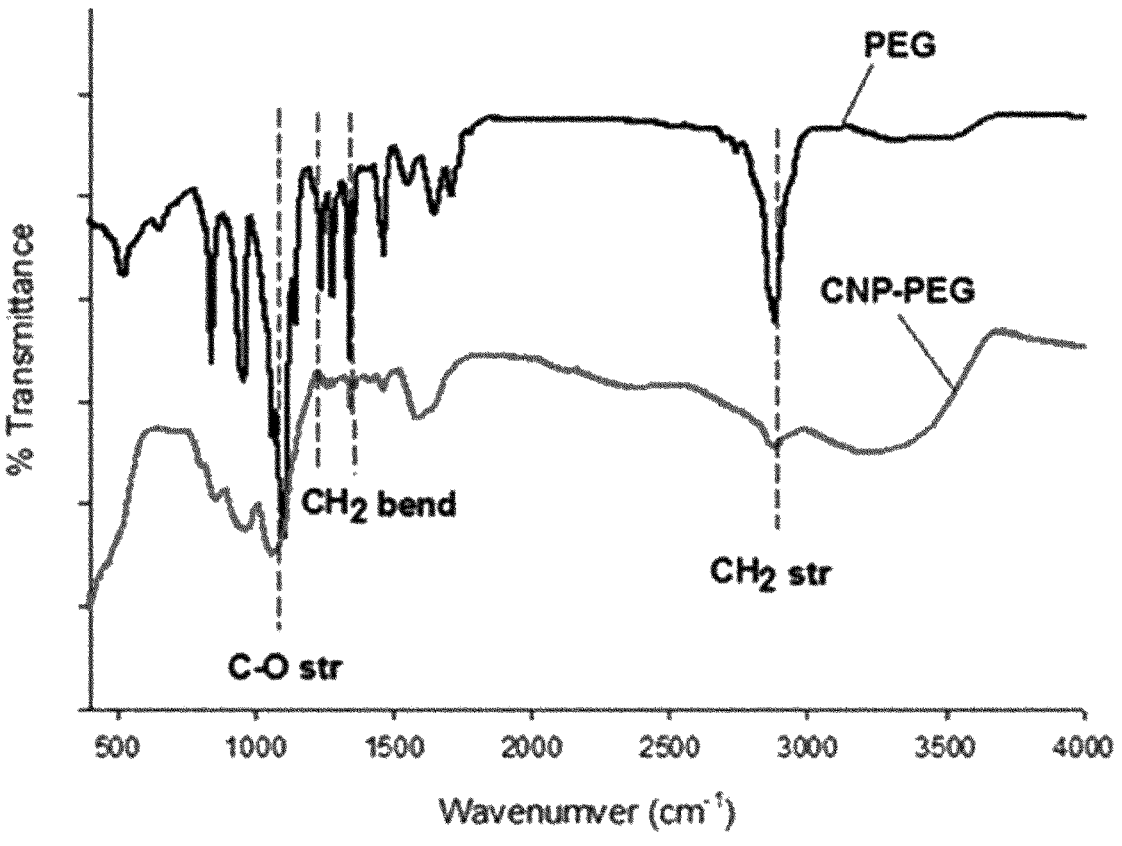
FIG. 2B shows a result of ATR-FTIR spectroscopy confirming the conjugation of cerium oxide nanoparticles and PEG.
Figure 3:
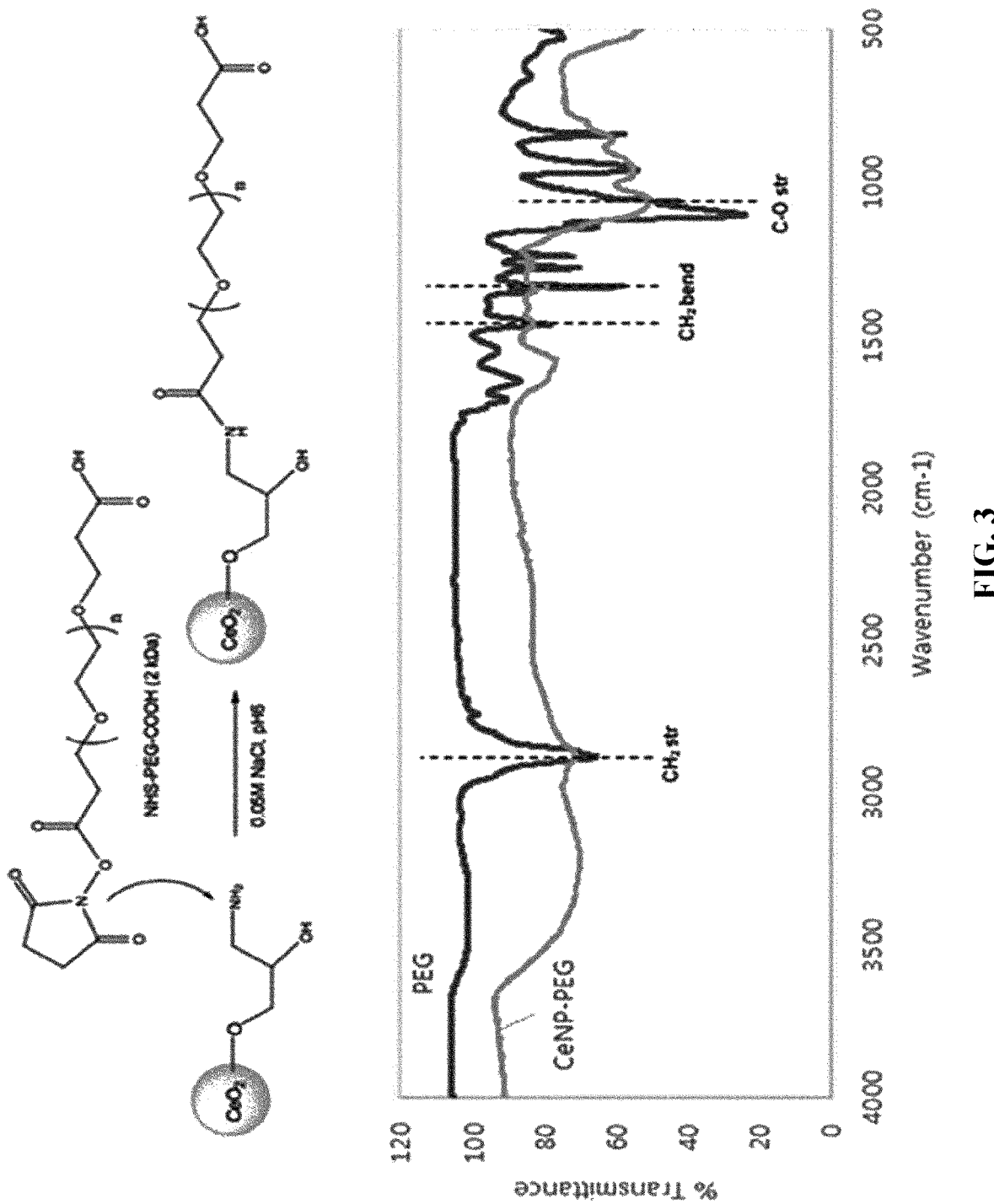
FIG. 3 schematically illustrates a process of introducing PEG to nanoparticles ($CeO_2$-PEG-COOH) according to the present invention, and a result of ATR-FTIR spectroscopy confirming the conjugation of cerium oxide nanoparticles and PEG.
Figure 4:
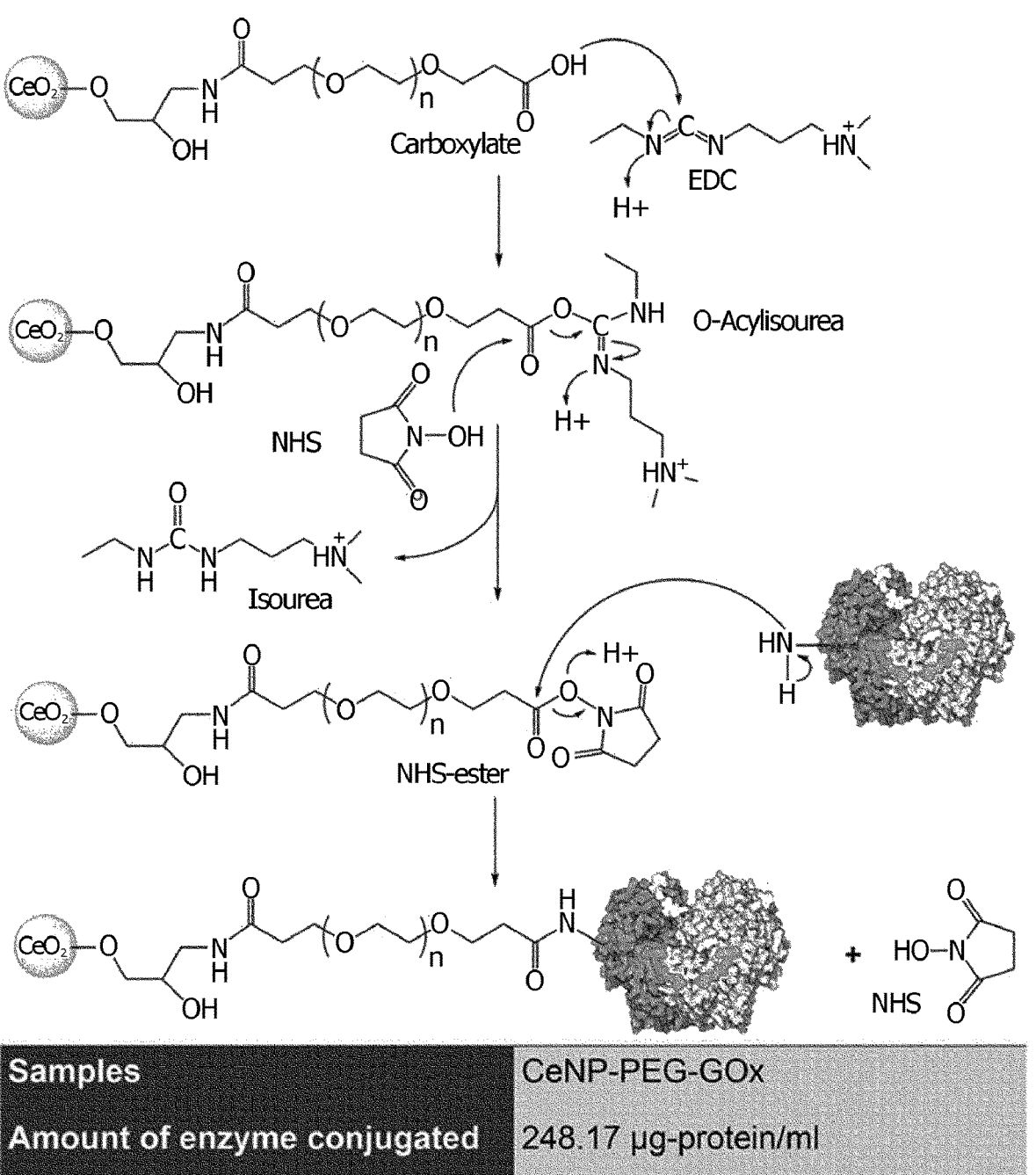
FIG. 4 schematically illustrates a process of conjugating glucose oxidase to nanoparticles ($CeO_2$-PEG-GOx) according to the present invention, and a result of BCA assay confirming the conjugation of glucose oxidase.

As a result, as shown in FIGS. 2 and 3, it was seen that, in the substituting process with an amine group, the ring of epichlorohydrin was open by shifting of the O peak of epichlorohydrin from 543.9 eV to 533.9 eV, thereby forming an amine group, and in $CeO_2$-PEG-COOH, PEG conjugation can be confirmed through CH$_2$ str (2900 cm$^{-1}$), CH$_2$ band (1300 to 1400 cm$^{-1}$) and C—O str peak (1100 cm$^{-1}$) (see FIG. 2A). Through IR spectroscopy, the conjugation between $CeO_2$ and PEG was confirmed again (see FIG. 2B), and the synthesis of the amine group or PEG-introduced CNPs was able to be confirmed (see FIG. 3). In addition, as shown in FIG. 4, in $CeO_2$-PEG-GOx, approximately 248.17 µg/ml of glucose oxidase was detected per 1 mg/ml of the complex, confirming that a sufficient amount of glucose oxidase (GOx) is conjugated to CNPs by means of PEG.

Figure 5A:
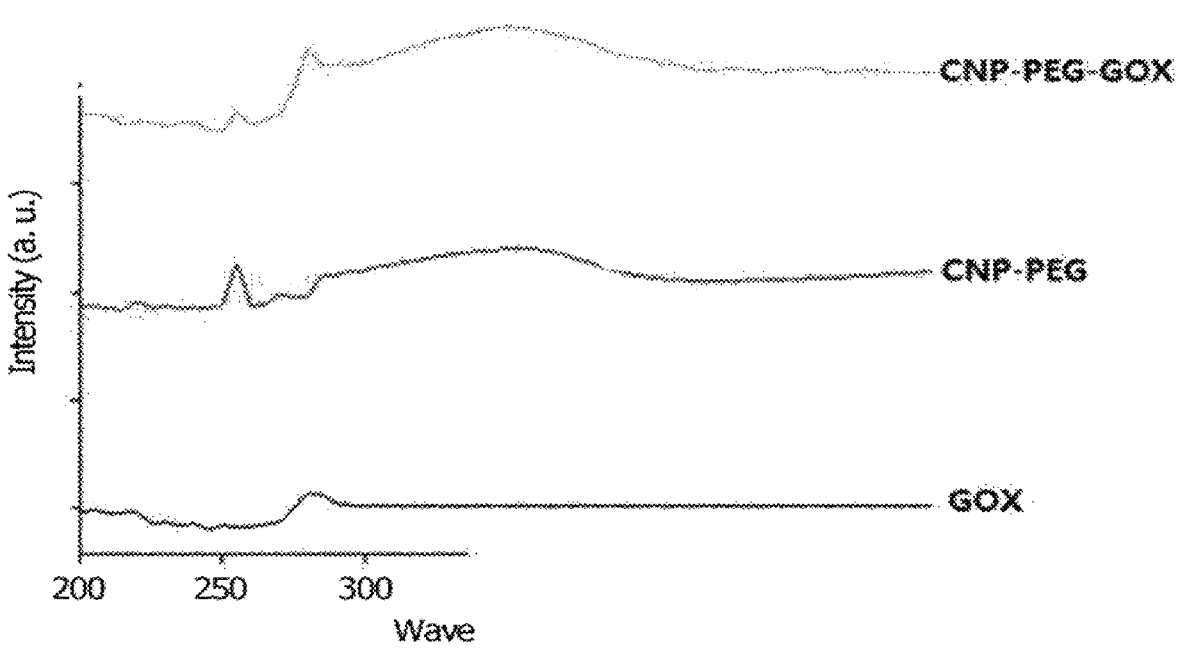
FIG. 5A shows absorbance spectra and FIG. 5B shows a result of SDS-PAGE confirming the synthesis of a complex for detecting glucose according to the present invention.
Figure 5B:
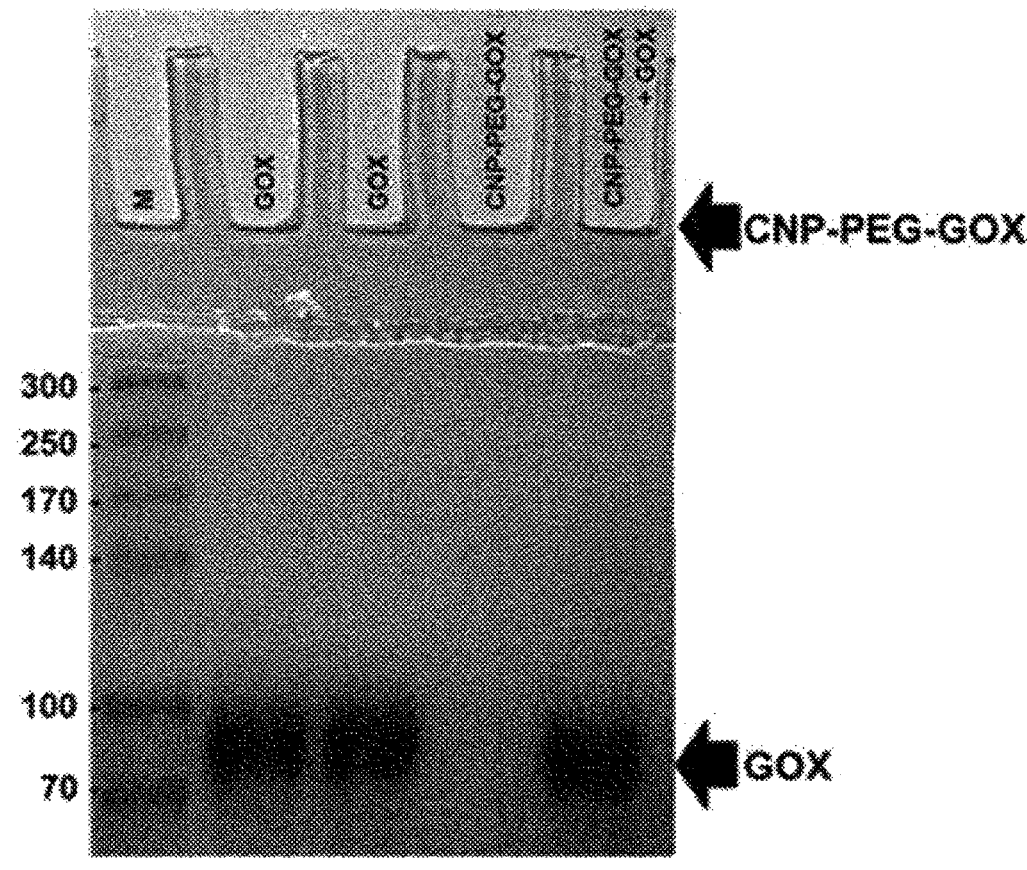

Meanwhile, as shown in FIG. 5, through the absorbance spectra, the synthesis of the $CeO_2$-PEG-GOx complex was verified (see FIG. 5A), and the complex for detecting glucose of the present invention was not loaded in a well of a stacking gel due to agglomeration, and the bands of lanes 1, 2 and 4, that is, protein bands exhibiting glucose oxidase were not detected (see FIG. 5B), suggesting a high purity of the complex for detecting glucose.

Example 2. Confirmation of Physical Properties of
CNP and Glucose Detection Through Colorimetric
Response In this example, the physical properties of CNPs, which is the main component of the complex for detecting glucose of Preparation Example 1, and colorimetric reactivity thereof were confirmed.

2-1. Confirmation of Physical Properties of CNP

The size and structure of CNPs ($CeO_2$ nanoparticles) according to Preparation Example 1 were confirmed using high-resolution transmission electron microscopy (HR-TEM), dynamic light scattering (DLS) and x-ray diffraction (XRD; reference; JCPDS 34-0394), and the ion proportion of CNPs was measured using x-ray photoelectron spectroscopy (XPS), thereby verifying the synthesis of the nanoparticle. In addition, an absorbance change by the reaction with hydrogen peroxide was observed, thereby confirming a change in activity of cerium ions in CNPs, shifting from $Ce^{3+}$ to $Ce^{4+}$.

Figure 6A:
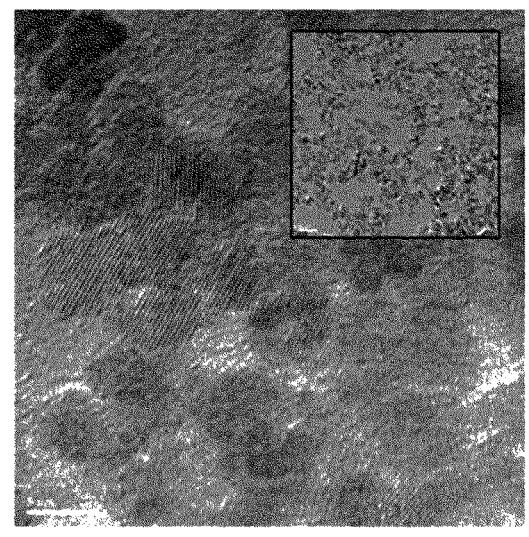
FIG. 6A is a HR-TEM result determining the size and structure of cerium oxide nanoparticles by examining the physical properties of the cerium oxide nanoparticles according to the present invention.
Figure 6B:
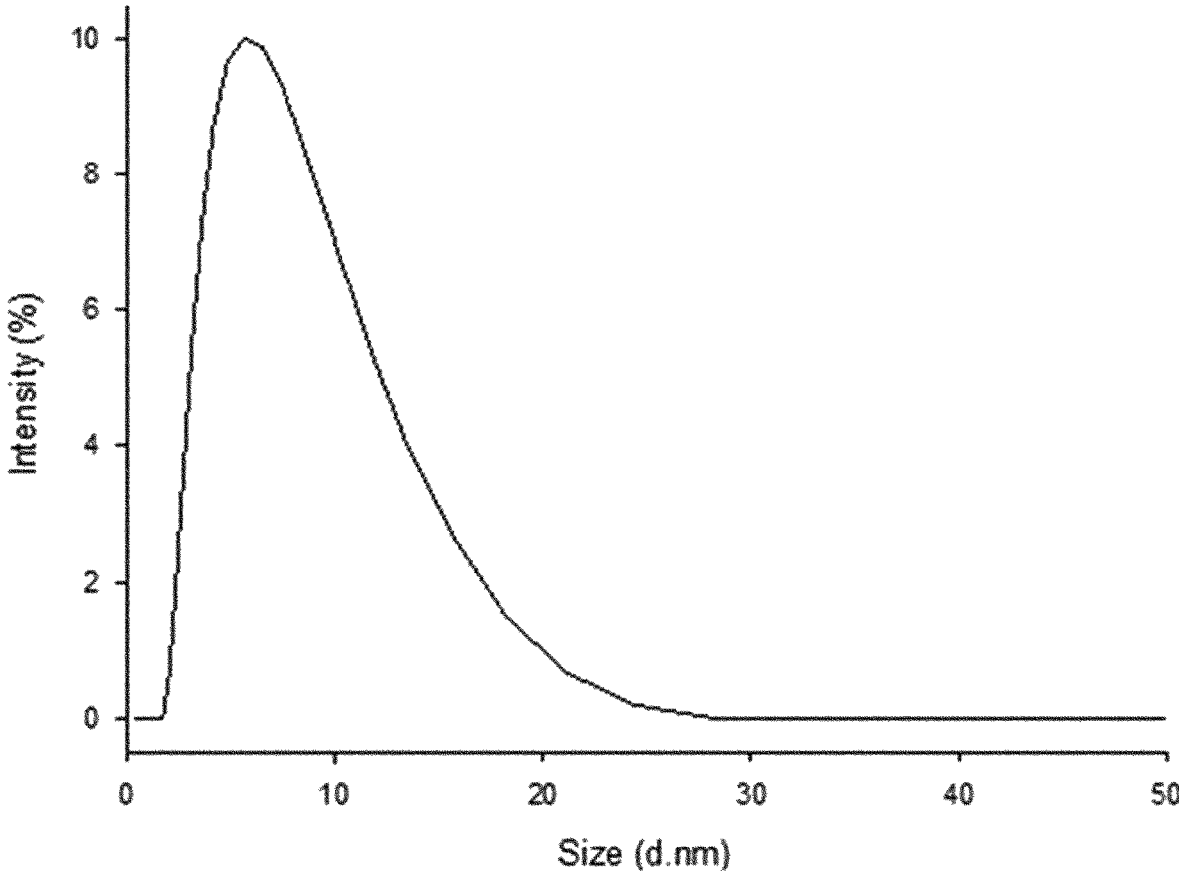
FIG. 6B is a DLS result determining the size and structure of cerium oxide nanoparticles by examining the physical properties of the cerium oxide nanoparticles according to the present invention.
Figure 6C:
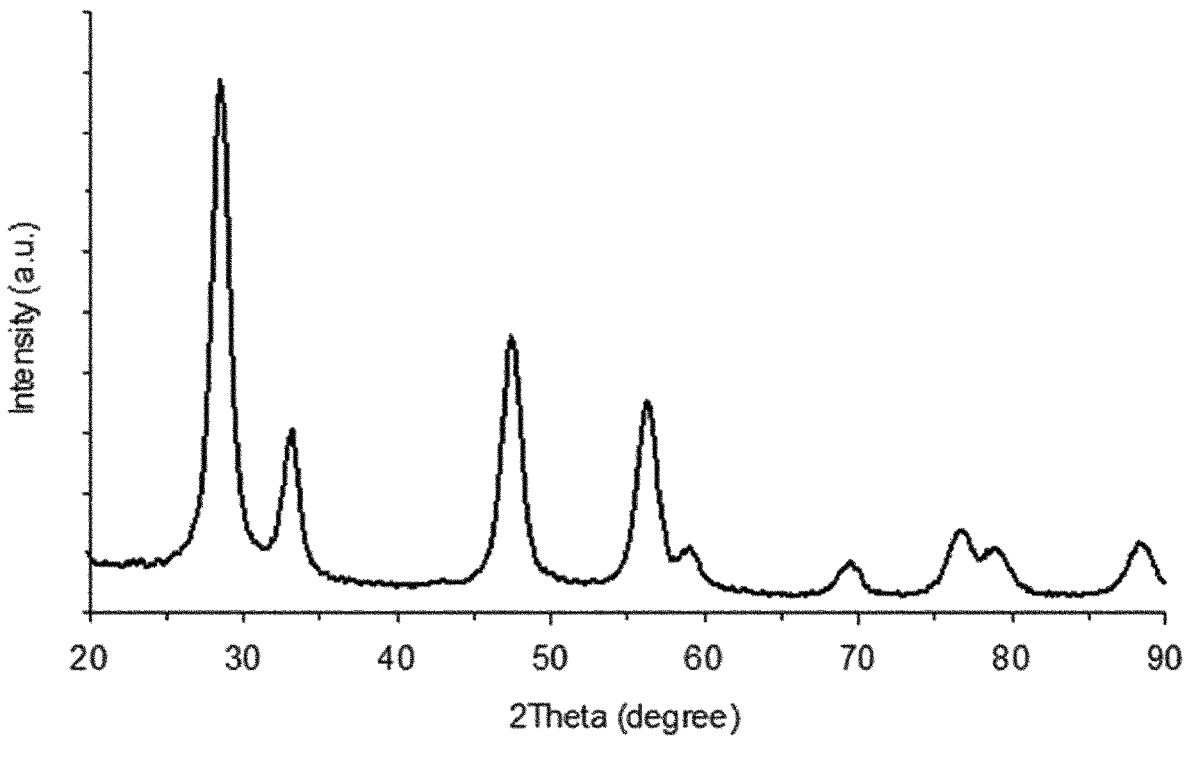
FIG. 6C is an XRD result determining whether cerium oxide nanoparticles are synthesized by examining the physical properties of the cerium oxide nanoparticles according to the present invention.
Figure 6D:
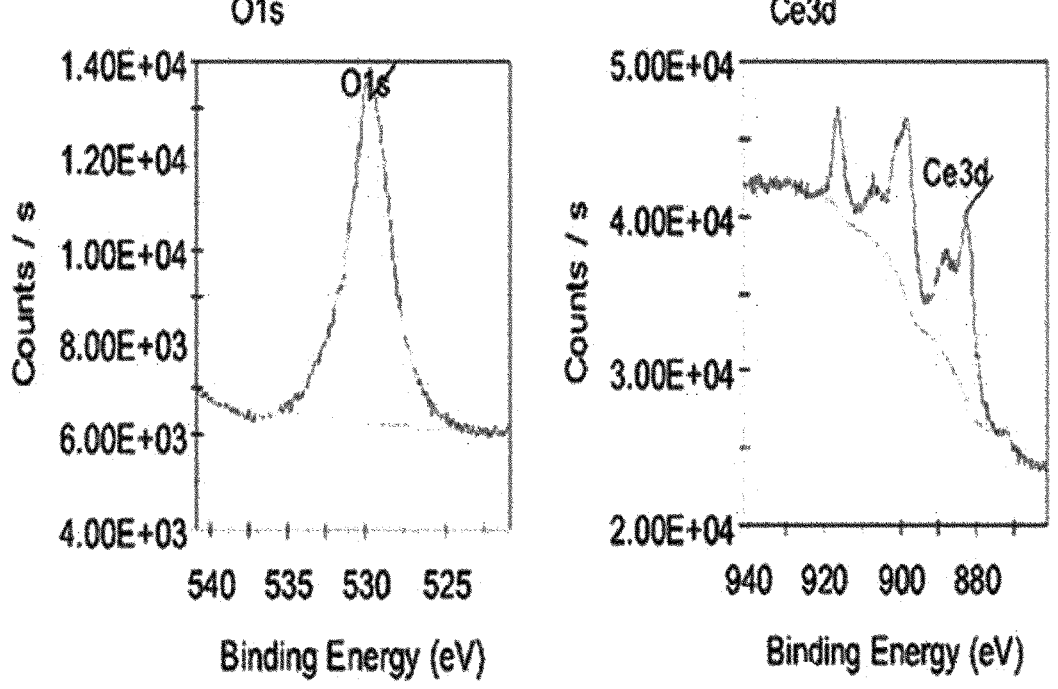
FIG. 6D is an XPS result determining whether cerium oxide nanoparticles are synthesized by examining the physical properties of the cerium oxide nanoparticles according to the present invention.
Figure 6E:
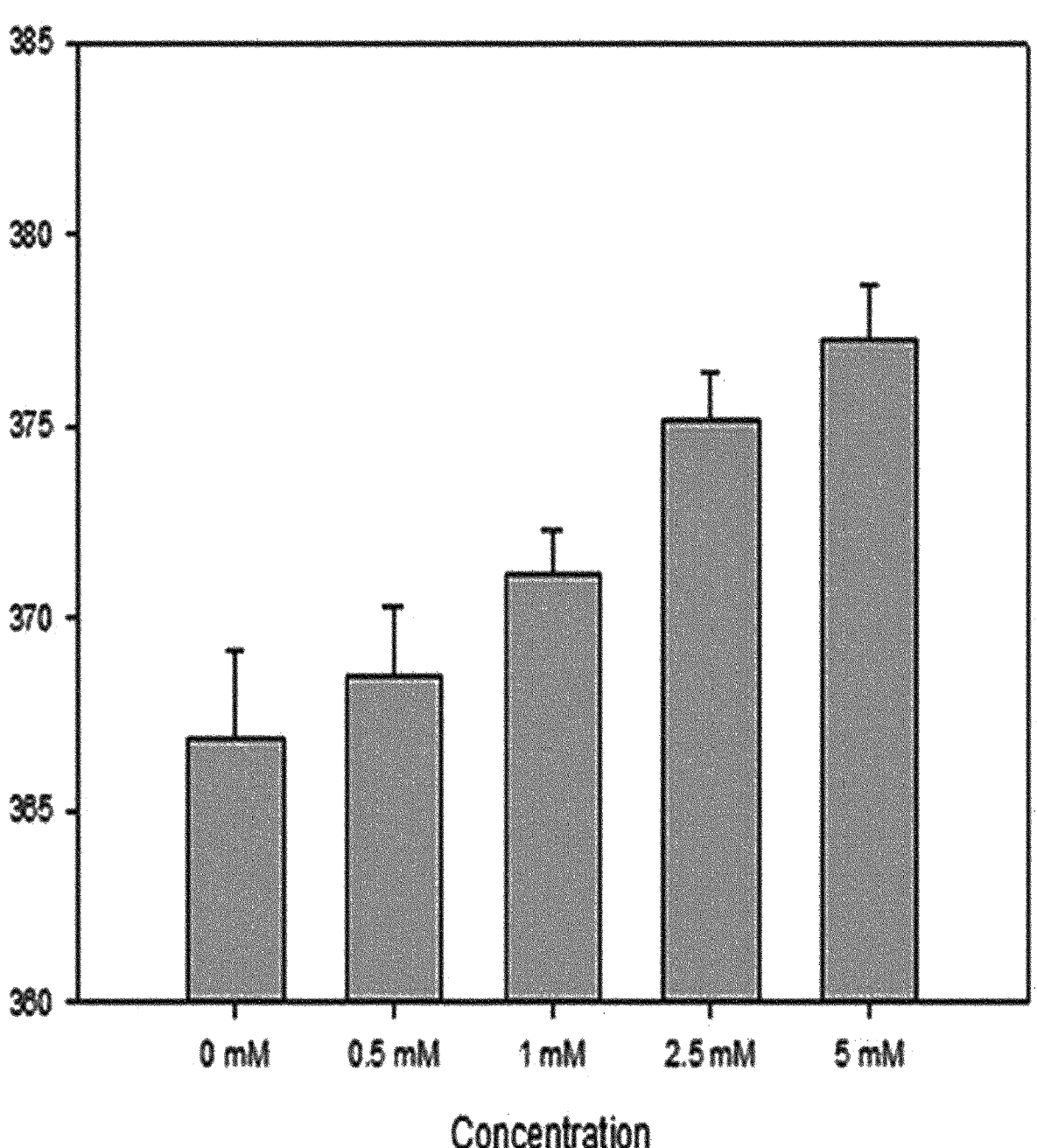
FIG. 6E is a result of confirming the activity of cerium ions in cerium oxide nanoparticles through an absorbance change by examining the physical properties of the cerium oxide nanoparticles according to the present invention.

As a result, as shown in FIG. 6, HR-TEM showed that the lattice structure of CNPs, which is the unique characteristic of the nanoparticle, was maintained, and the nanoparticle has a diameter of approximately 6 to 7 nm (see FIGS. 6A and 6B). In addition, peaks corresponding to the Reference peak were detected, and O1s and Ce3ds showed atomic percentages of 62.24% and 37.76%, respectively, indicating CNP synthesis (see FIGS. 6C and 6D). It was confirmed that, as the concentration of hydrogen peroxide increases (0, 0.5, 1, 2.5 and 5 mM), $Ce^{4+}$ in CNPs increases, indicating that the activity of cerium oxide is maintained despite the formation of a nanoparticle (see FIG. 6E).

2-2. Confirmation of Glucose Detection of CNT Through Colorimetric Method

First, colorimetric reactions of 1 w/v % CNPs with various concentrations (0, 0.5, 1, 2.5, 5 mM) of hydrogen peroxide were confirmed, and based on the reactions, it was attempted to confirm whether the nanoparticle can have a colorimetric reaction with hydrogen peroxide generated from glucose. Specifically, 1 w/v % CNPs was mixed with 100 U/ml of glucose oxidase (GOx), various concentrations (0, 0.5, 1, 2.5 and 5 mM) of glucose were added and reacted for approximately 2 minutes to confirm a colorimetric reaction of CNPs. RGB color intensity analysis (B value) was performed to confirm the relationship between the color intensity of CNPs and a glucose concentration.

In addition, RGB color intensity analysis (RGB values) was performed on various concentrations (0, 0.1, 0.25, 0.5, 1 and 2 w/v %) of CNPs according to the change in hydrogen peroxide or glucose concentration (0, 0.1, 0.2, 0.4 and 0.6 mM) to deduce a concentration of CNPs capable of quantitatively analyzing a glucose concentration according to color intensity.

Figure 7:
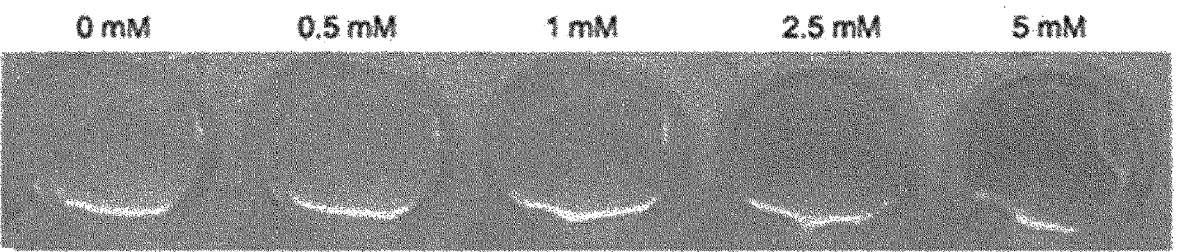
FIG. 7 shows a visual observation result of detecting a colorimetric reaction after cerium oxide nanoparticles (1 w/v %) according to the present invention react with various concentrations (0, 0.5, 1, 2.5 and 5 mM) of hydrogen peroxide.
Figure 8A:
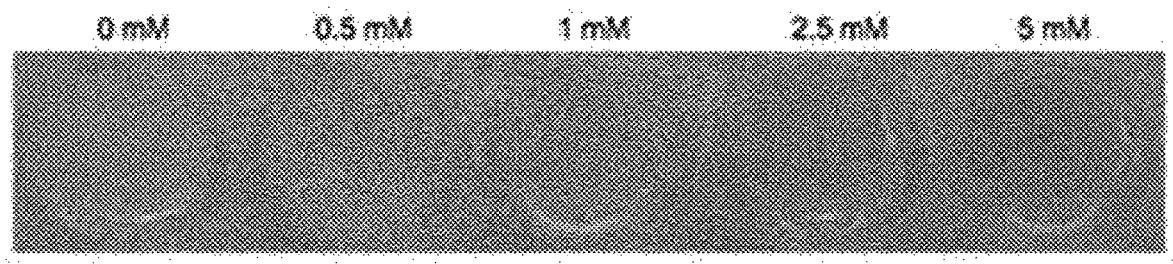
FIG. 8A shows a visual observation result of detecting a colorimetric reaction and FIG. 8B shows a color intensity analysis (B value) result after cerium oxide nanoparticles (1 w/v %) according to the present invention react with glucose oxidase and various concentrations (0, 0.5, 1, 2.5 and 5 mM) of glucose.
Figure 8B:
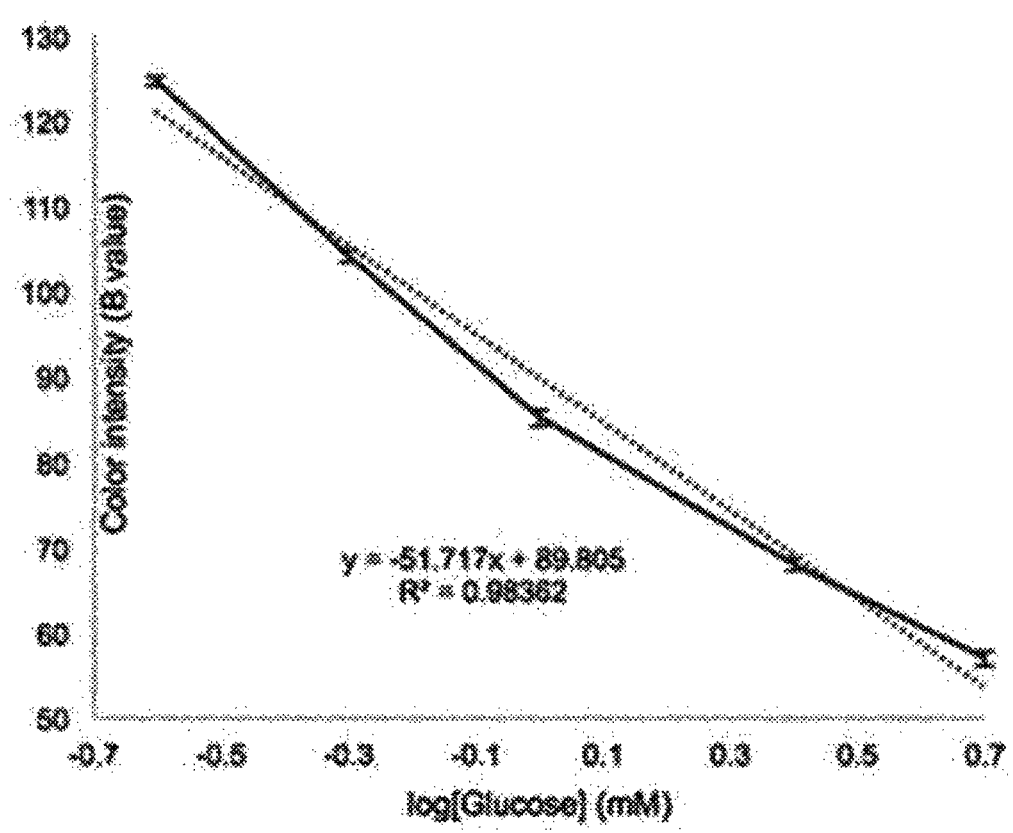

As a result, as shown in FIG. 7, the CNPs according to the present invention was immediately colored after treatment with hydrogen peroxide at a concentration of approximately 0.5 mM or more. In addition, FIG. 8 showed that CNPs was sufficiently colored with respect to hydrogen peroxide generated in a glucose degradation process with glucose oxidase (see FIG. 8A), and such color intensity (B value) was highly correlated with glucose concentration (linear correlation; $R^2=0.98$) (see FIG. 8B). In other words, it can be seen that a product of glucose oxidase can be quantitatively measured through the colorimetric reaction of CNPs, resulting in effective detection of a glucose concentration.

Figure 9A:
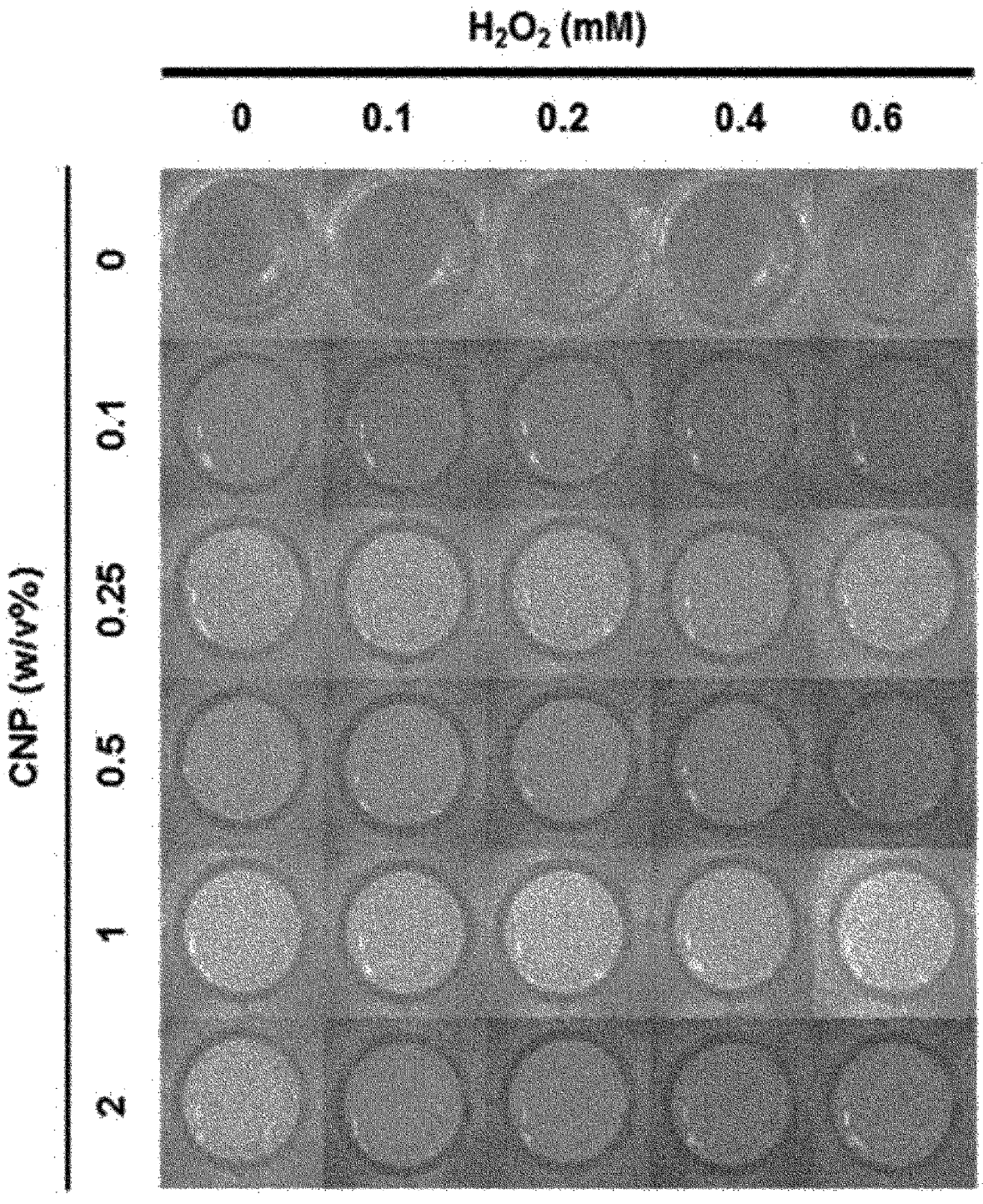
FIG. 9A shows a visual observation result of detecting a colorimetric reaction after the cerium oxide nanoparticles according to the present invention (0, 0.1, 0.25, 0.5, 1 or 2 w/v %) react with various concentrations (0, 0.1, 0.2, 0.4 and 0.6 mM) of hydrogen peroxide.
Figure 9B:
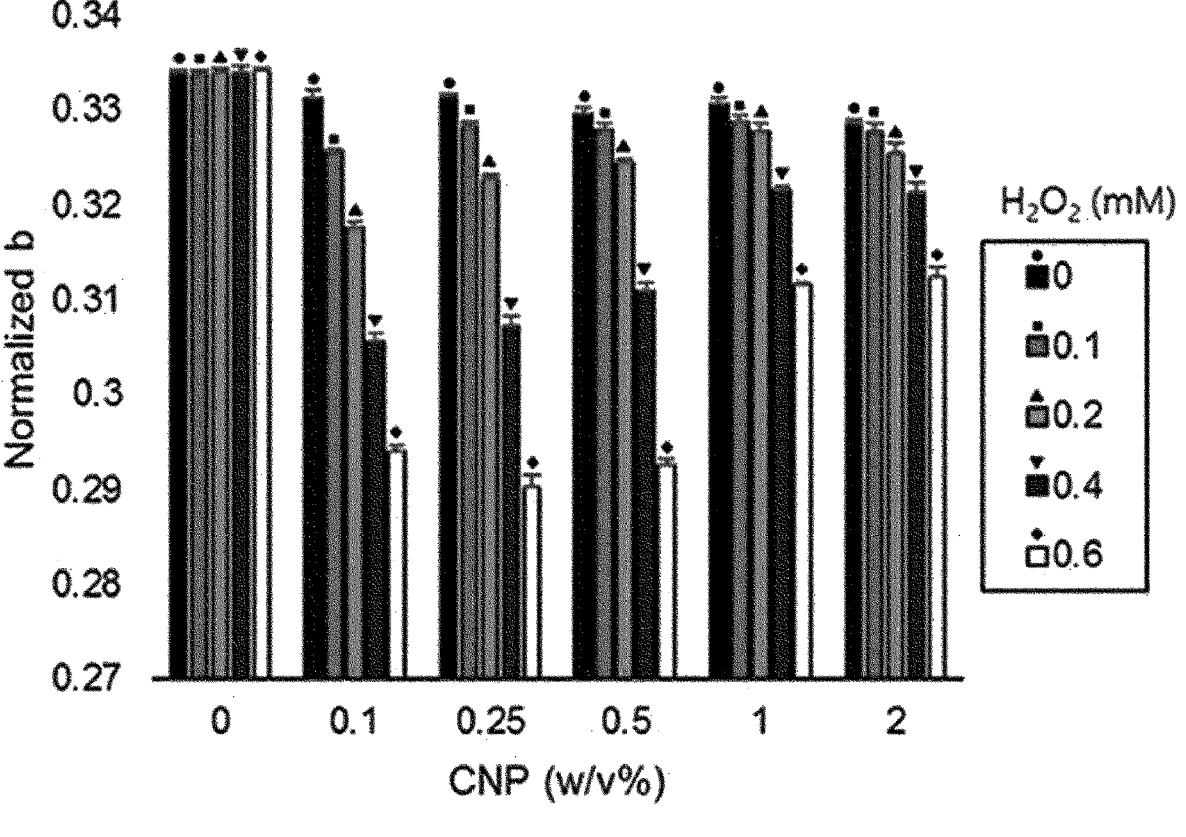
FIG. 9B shows a result of color intensity analysis (RGB values) after cerium oxide nanoparticles according to the present invention (0, 0.1, 0.25, 0.5, 1 and 2 w/v %) react with various concentrations (0, 0.1, 0.2, 0.4 and 0.6 mM) of hydrogen peroxide.
Figure 10A:
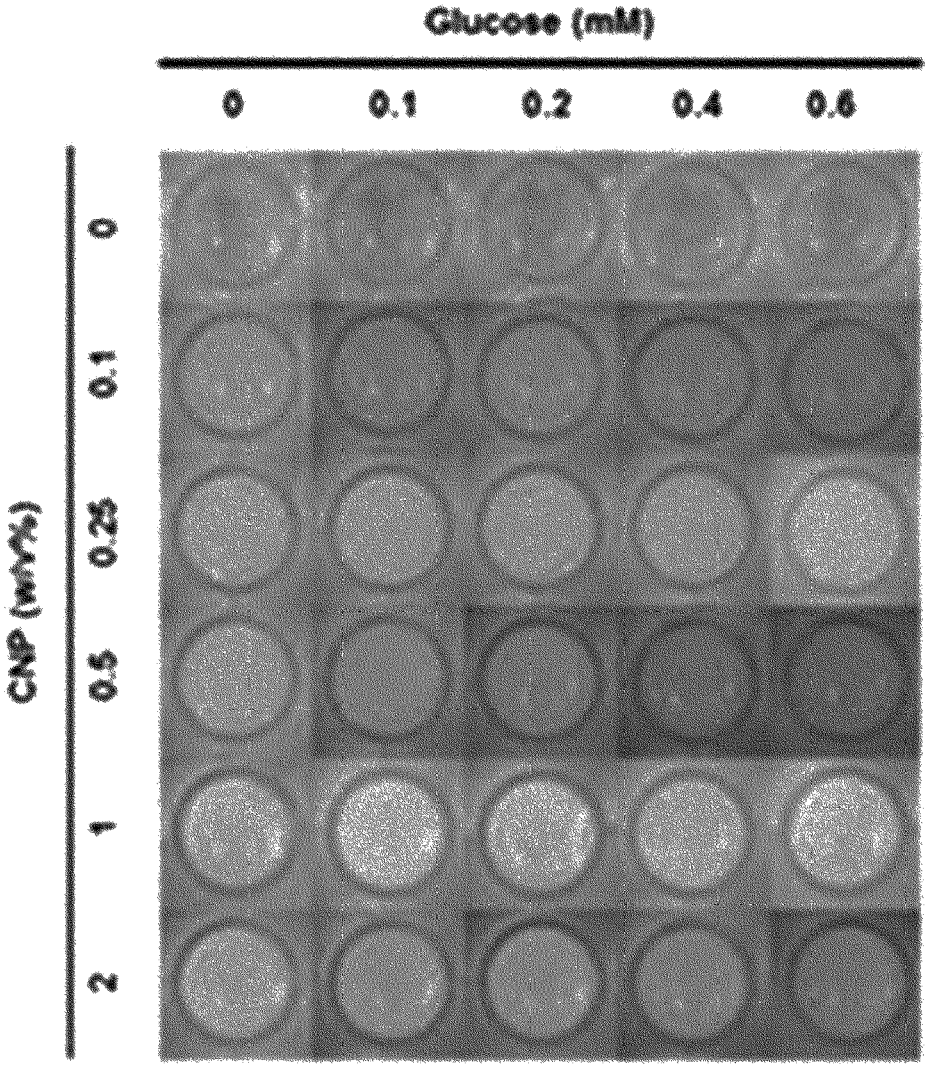
FIG. 10A shows a visual observation result of detecting a colorimetric reaction after cerium oxide nanoparticles (0, 0.1, 0.25, 0.5, 1 or 2 w/v %) according to the present invention react with various concentrations (0, 0.1, 0.2, 0.4 and 0.6 mM) of glucose.
Figure 10B:
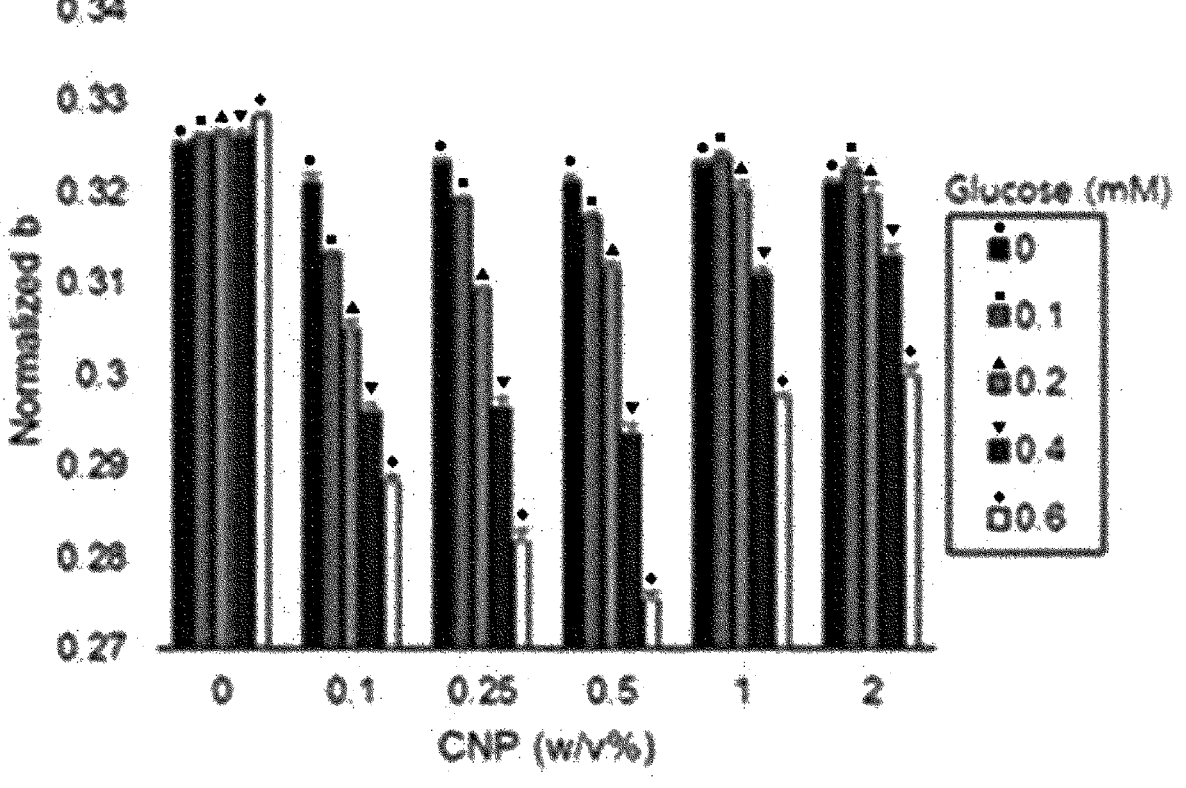
FIG. 10B shows a result of color intensity analysis (RGB values) after cerium oxide nanoparticles (0, 0.1, 0.25, 0.5, 1 or 2 w/v %) according to the present invention react with various concentrations (0, 0.1, 0.2, 0.4 and 0.6 mM) of glucose.

In addition, as shown in FIGS. 9 and 10, the same as the above-described result, it was confirmed that the change in color intensity (RGB values) of CNT can be confirmed by the change in hydrogen peroxide or glucose concentration, and particularly, when a CNP concentration is 0.5 w/v % or less, there was a significant difference in color intensity according to a glucose concentration.

Example 3. Confirmation of Colorimetric Reaction of Complex for Detecting Glucose In this example, it was attempted to confirm whether a $CeO_2$-PEG-GOx complex is colored according to a glucose concentration, like Example 2-2. Specifically, the complex was reacted with various concentrations (0, 0.25, 0.5, 1 and 2.5 mM) of glucose to see a colorimetric reaction thereby, and RGB color intensity analysis (B value or RGB values) was performed. To confirm selective reactivity to glucose, the $CeO_2$-PEG-GOx complex was treated with various types of carbohydrates (fructose, galactose and sucrose), and then RGB color intensity analysis (RGB values) was performed for each sample.

Figure 11A:
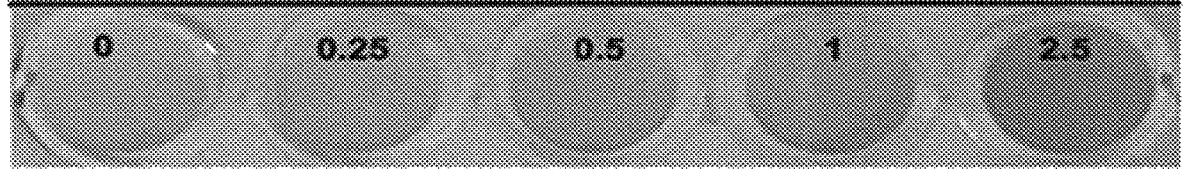
FIG. 11A shows a visual observation result of detecting a colorimetric reaction and FIG. 11B shows a result of color intensity analysis (RGB values) after a complex for detecting glucose according to the present invention reacts with various concentrations (0, 0.25, 0.5, 1 and 2.5 mM) of glucose.
Figure 11B:
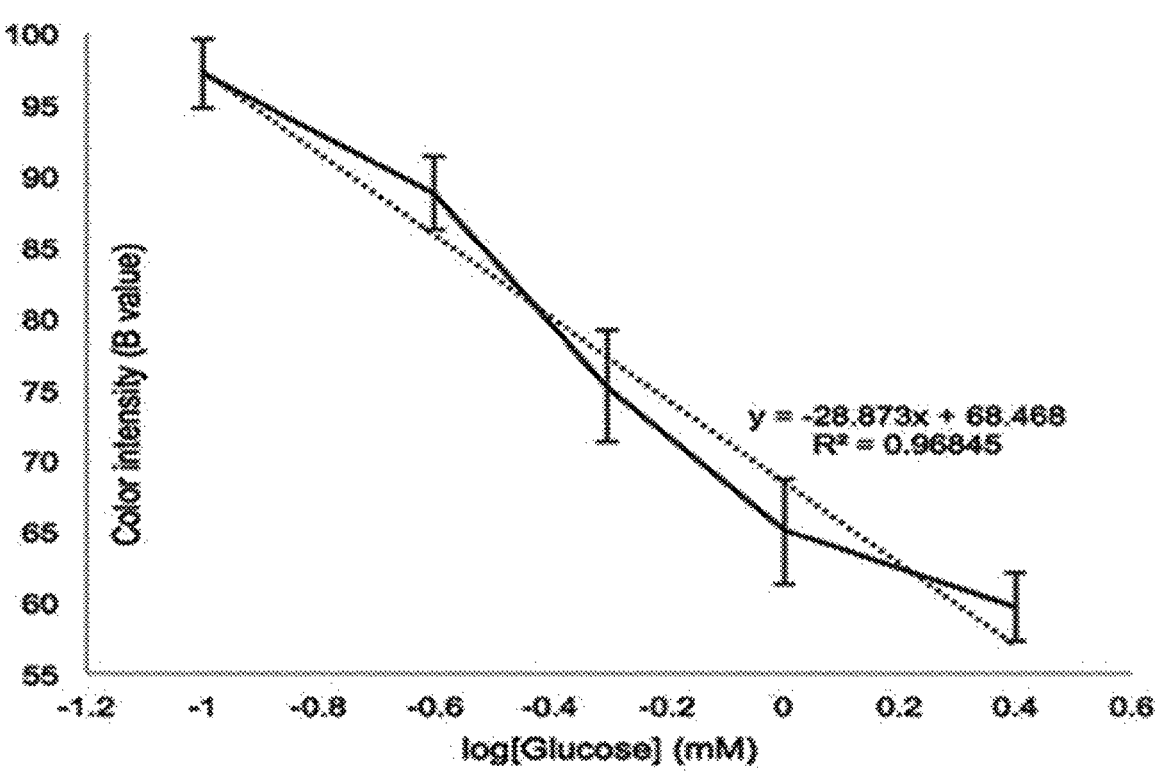
Figure 12A:
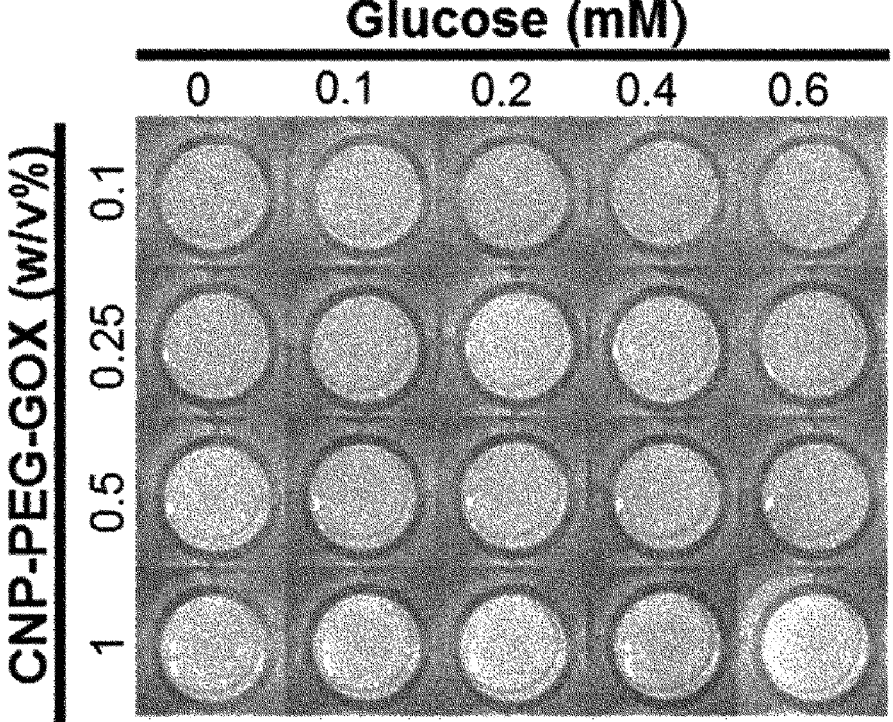
FIG. 12A shows a visual observation result of detecting a colorimetric reaction after a complex for detecting glucose (0.1, 0.25, 0.5 or 1 w/v %) according to the present invention reacts with various concentrations (0, 0.1, 0.2, 0.4 and 0.6 mM) of glucose.
Figure 12B:
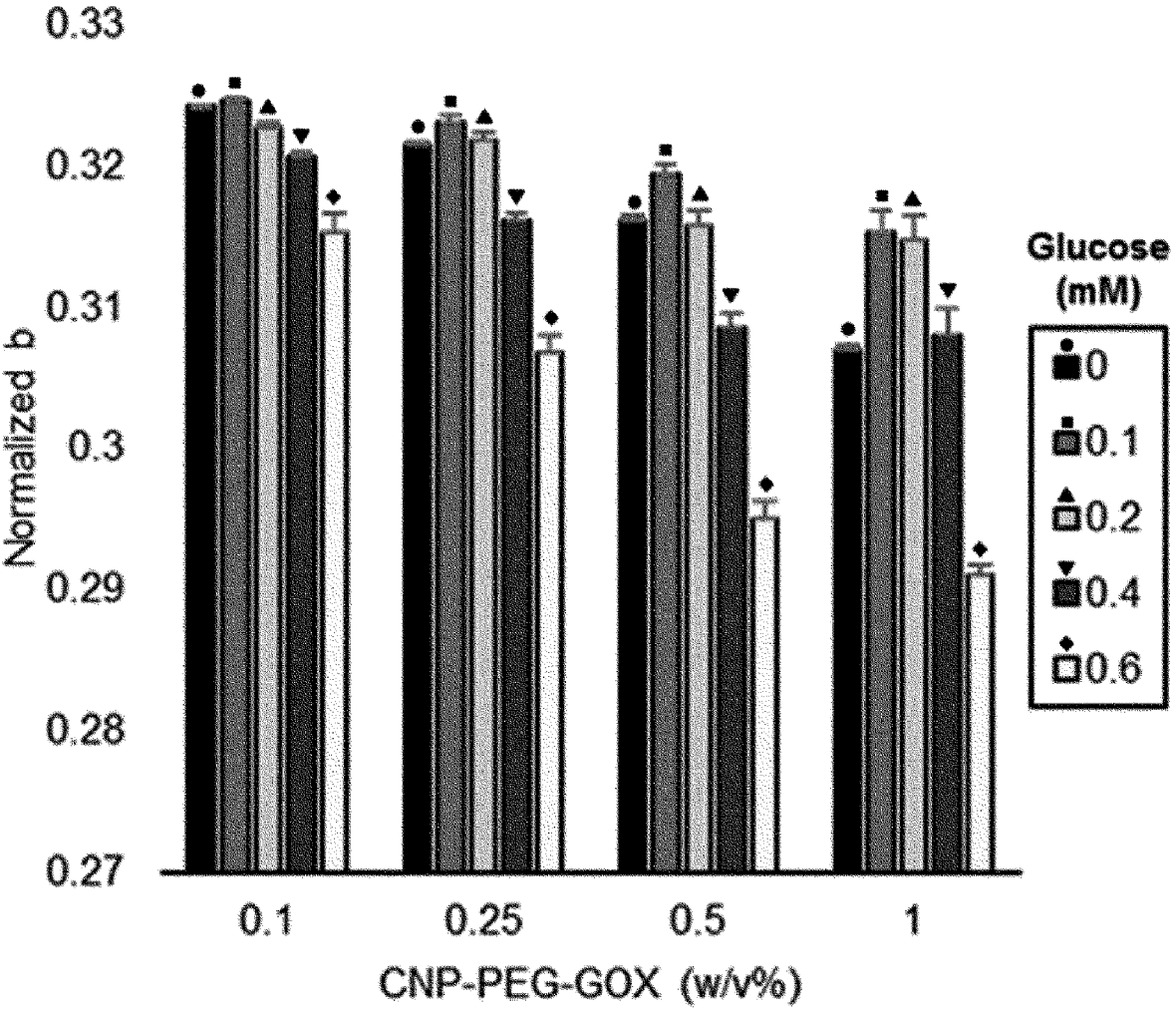
FIG. 12B shows a result of color intensity analysis (RGB values) after a complex for detecting glucose (0.1, 0.25, 0.5 or 1 w/v %) according to the present invention reacts with various concentrations (0, 0.1, 0.2, 0.4 and 0.6 mM) of glucose.

As a result, as shown in FIG. 11, it can be seen that the $CeO_2$-PEG-GOx complex reacted with various concentrations (0. 0.25, 0.5 and 0.25 mM) of glucose to exhibit color, and as described above, it can be seen that the color intensity (B value) is linearly correlated with glucose concentration ($R^2=0.97$). In addition, as shown in FIG. 12, even when measured with RGB values, the $CeO_2$-PEG-GOx complex exhibited a significant difference in color intensity with respect to various concentrations (0. 0.1, 0.2, 0.4 and 0.6 mM) of glucose.

In addition, as shown in FIG. 13, a significant change in color intensity of the $CeO_2$-PEG-GOx complex was only observed in a glucose-treated group, confirming high selectivity for glucose. From this result, it can be seen that the $CeO_2$-PEG-GOx complex according to the present invention can be used in quantitative, specific glucose detection.

Example 4. Confirmation of Physical Properties of Contact Lens-Type Sensor for Detecting Glucose In this example, it was attempted to confirm the physical properties of the contact lens-type sensor for detecting glucose of Preparation Example 2. First, the appearance of the contact lens-type sensor including a 1 w/v % $CeO_2$-PEG-GOx complex was visually observed, and the equilibrium water content (EWC) thereof was calculated by the following Formula 1.

$$W_s - W_d / W_s \, 100 = \quad \text{equilibrium water content } (EWC)$$

[Mathematical Formula 1]

($W_s$: water content before drying, $W_d$: water content after drying)

In addition, by comparing diameters and heights before and after drying between a general pHEMA contact lens and the contact lens-type sensor according to the present invention, structural changes were confirmed, and the concentration of the $CeO_2$-PEG-GOx complex in the contact lens-type sensor having suitable physical properties, which can be directly applied to an eyeball, was deduced by measuring the change in elastic modulus depending on the concentration (1 or 10 w/v %) of the $CeO_2$-PEG-GOx complex.

As a result, as shown in FIGS. 14 and 15, as the contact lens-type sensor according to the present invention contains the $CeO_2$-PEG-GOx complex, the contact lens-type sensor was slightly semi-transparent, but still had a contact lens shape formed by a mold or elasticity (see FIGS. 14A and 14B), and EWC of the contact lens-type sensor was 38.2%, corresponding to within the EWC range of 38 to 40% of the general pHEMA contact lens. In addition, since the contact lens contains water, there were changes in diameter and height before and after drying, and there was almost no difference between the pHEMA contact lens and the contact lens-type sensor of the present invention (see FIG. 15). Through the above results, it was confirmed that, even when the $CeO_2$-PEG-GOx complex was contained, there was almost no structural difference in the contact lens.

In addition, as shown in FIG. 16, compared with the pHEMA contact lens, as the contact lens-type sensor including a 1 w/v % $CeO_2$-PEG-GOx complex is slightly decreased in elastic modulus, it was considered to have increased wearability and reduced mechanically-induced ocular complications. However, since the contact lens-type sensor including a 10 w/v % $CeO_2$-PEG-GOx complex has an excessively large amount of the complex, it can be confirmed that an elastic modulus is greatly increased, compared with the pHEMA contact lens. Through the above results, it can be seen that the contact lens-type sensor including the 1 w/v % $CeO_2$-PEG-GOx complex has suitable physical properties as a contact lens which can be directly applied to an eyeball.

In addition, as a result of observing the change in the contact lens-type sensor according to contents (115, 230, 465 and 930 μg/lens) of the $CeO_2$-PEG-GOx complex, as shown in FIG. 17, it can be confirmed that lens transparency was reduced by an increase in the content of the complex, suggesting that a suitable amount of the $CeO_2$-PEG-GOx complex should be included in the contact lens-type sensor.

Example 5. Confirmation of Colorimetric Reaction of Contact Lens-Type Sensor for Detecting Glucose In this example, it was attempted to confirm whether a contact lens-type sensor for detecting glucose was colored according to a concentration of glucose. First, when various concentrations (1 to 10 mM) of glucose were reacted with the contact lens-type sensor in a buffer solution, a colorimetric reaction thereby was confirmed, and RGB color intensity analysis was performed. In addition, as described above, various concentrations (0.2 to 2 mM) of glucose were reacted in the same manner as described above under an artificial tear condition, and then RGB color intensity analysis (B value) was performed. Meanwhile, Eyemiru Contact Pure Eye Drops (CJ, Korea), which does not contain a preservative, was used as artificial tears.

As a result, as shown in FIGS. 18 and 19, it was confirmed that, under both buffer and artificial tear conditions, color intensity was increased by an increase in glucose concentration, suggesting a linear correlation between glucose concentration and color intensity (buffer; $R^2=0.98$, artificial tears; $R^2=0.96$). Particularly, considering that the tear glucose level of a normal person is approximately 0.1 to 0.4 mM, and the tear glucose level of a diabetic patient is approximately 0.5 to 1.0 mM, glucose in the concentration range from approximately 0.2 to 2 mM can be detected through a quantitative colorimetric reaction under an artificial tear condition, showing that the contact lens-type sensor can be effectively applied in glucose detection or diabetic diagnosis for a diabetic patient or a suspected diabetic patient.

In addition, to improve visibility through the CNP-PEG-GOx-laden contact lenses, center-transparent contact lenses with CNPPEG-GOx loaded only at the edges were designed (FIG. 20A, inset photograph). It reacted with glucose and changed the color, but the reaction time increased with the increase in thickness (FIG. 20A). Moreover, it was confirmed that the increase of the thickness does not maintain proper lens characteristics (FIG. 20B). It is expected that the problems would be solved through factory-level production later.

Example 6. Confirmation of Detection Efficiency According to Concentration of Complex in Contact Lens-Type Sensor for Detecting Glucose In this example, it was attempted to deduce an optimal concentration of a complex for detecting glucose in a contact lens-type sensor for detecting glucose. Specifically, a contact lens-type sensor including a 0.1, 0.25, 0.5, 1 or 2% (w/v) complex for detecting glucose was produced, and then a color change in the sensor for various concentrations (0, 0.01, 0.05, 0.1, 0.2, 0.3, 0.4 and 0.5 mM) of glucose were observed.

In addition, the change in color intensity (RGB values) of a sensor according to the reaction between the contact lens-type sensor for detecting glucose, which includes various amounts (115, 230, 465 and 930 μg/lens) of the $CeO_2$-PEG-GOx complex and a constant concentration of glucose (0.6 mM) were observed according to time, followed by observing the change in color intensity (RGB values) of the sensor according to the change in glucose level in buffer or artificial tears.

As a result, as shown in FIG. 21, it can be confirmed that, under a glucose concentration ranging from 0.01 mM to 0.5 mM, the color of the contact lens-type sensor which was colorless changed to yellow depending on a concentration, and was evenly exhibited all over the contact lens. In addition, considering that as a color difference according to the glucose concentration is more distinct, more accurate measurement is possible, it can be seen that a concentration of the glucose complex in the contact lens-type sensor is at least 0.5% (w/v).

In addition, as shown in FIG. 22, when reacting with a constant concentration of glucose, constant color intensity was exhibited in a content range of 250 to 1000 μg/lens of the $CeO_2$-PEG-GOx complex, and as shown in FIGS. 23 and 24, it can be confirmed that, in both buffer or artificial tears, color intensity of the contact lens-type sensor according to the present invention was changed in accordance with a change in glucose concentration.

Example 7. Confirmation of Stability of Contact Lens-Type Sensor for Detecting Glucose In this example, to confirm the possibility of long-term storage, it was attempted to confirm stability of a contact lens-type sensor for detecting glucose in a solution. After the contact lens-type sensor was stored in a 0.9% NaCl solution for 1 month, its structural change was not only observed by the naked eye, but also the presence of CNPs in the solution was examined through UV-Vis spectroscopy.

As a result, as shown in FIG. 25, after one month, the structure of the contact lens-type sensor was still maintained, and no peak at 245 nm, indicating cerium oxide, was observed, indicating no release of CNPs into the solution. From the results, it can be seen that the contact lens-type sensor according to the present invention has excellent stability such that it can be stored in a solution for a long period of time.

Example 8. Cytotoxicity Testing for Contact Lens-Type Sensor for Detecting Glucose In this example, it was attempted to evaluate the toxicity of a contact lens-type sensor for detecting glucose, and cytotoxicity was evaluated for human umbilical vein endothelial cells (HUVECs) using a Cell Counting Kit-8 (CCK-8). First, the cells were treated with various concentrations of a $CeO_2$-PEG-GOx complex (1 to 10000 μg/ml) for 24, 48 and 72 hours, and then respective cell survival rates were evaluated. In addition, the contact lens-type sensor including the 1% (w/v) complex for detecting glucose was cut to a diameter of 5 mm, followed by (A) being cultured with the cells for 24 hours; (B) being put into an insert of a 24-well insert plate and then cultured with the cells for 24 hours; or (C) being cultured in a separate medium and then added to a medium containing the cells for evaluating cytotoxicity for each sample (see FIG. 27A). As comparative groups, a group in which the sensor is not treated, and a group in which a HEMA contact lens not containing a complex for detecting glucose is treated were used.

As a result, as shown in FIG. 26, when a concentration of the $CeO_2$-PEG-GOx complex is 20 μg/ml or less, despite the passage of time, no significant decrease in cell survival rate was observed. In addition, as shown in FIG. 27, when the cells were cultured with the contact lens-type sensor for detecting glucose according to the present invention, compared with the control groups, no significant decrease in the number of viable cells was shown, and in the other groups, like the above result, no significant cytotoxicity was observed. From the above results, it can be seen that the contact lens-type sensor according to the present invention has excellent biocompatibility.

Example 9. Glucose Detection and Quantification Using Animal Model

In this example, a colorimetric reaction of the contact lens-type sensor for detecting glucose of the present invention was examined for animal models (rabbits) in which high blood pressure was temporarily induced, and a glucose concentration was quantified based on the above results. Specifically, the contact lens-type sensor was worn on an eyeball of the animal model for 30 minutes and then removed, followed by RGB color intensity analysis (RGB values) for the contact lens-type sensor.

As a result, as shown in FIG. 28, after 30 minutes, it can be seen that the transparency of the contact lens-type sensor for detecting glucose was considerably decreased, and a significant change in color intensity was confirmed. In addition, as shown in FIG. 29, based on the conventional formula defining the relationship between a tear glucose level and color intensity, the tear glucose level was able to be estimated from normalized RGB values. Therefore, the contact lens-type sensor according to the present invention may not only detect a glucose concentration in the body by a non-invasive and effective method, but also provide quantitative data for glucose concentrations in the body through color intensity analysis.

Comparative Example. Reliability of CNP-PEG-GOx-Laden Contact Lenses with Human Tear Specimens Next, we evaluated the reliability of the CNP-PEG-GOx-laden contact lenses using tear specimens from human volunteers. Tear specimens were collected from 10 volunteers (5 diabetic patients and 5 healthy persons) using capillary tubes. The collected volume of each tear specimen was 5-10 ul, which was insufficient to wet an entire contact lens (18-21 mm in diameter). Therefore, to analyze the tiny volume of our tear specimens, we fabricated smaller CNP-PEG-GOx-laden contact lenses (approximately 3 mm in diameter). Furthermore, we needed to improve our image acquisition system and calculation algorithm to accommodate the smaller contact lens before and after incubation with glucose. We configured the image acquisition system using a zoom lens and color CCD to analyze the general RGB profile on colorimetric CNP-PEG-GOx-laden contact lenses wet with tear specimens. After that, the central area (0.5 $mm^2$) of each acquired image was cropped and analyzed using an intensity normalization process. To further normalize the normalized rgb color profile on the small colorimetric CNP-PEG-GOx-laden contact lenses, the difference value was calculated before and after incubation with the tear specimens. When glucose samples were incubated with the small CNP-PEG-GOx-laden contact lenses, the difference value of the normalized b ($\Delta b$) was used to monitor the different glucose concentrations (Table 1). These results indicate that our small-volume tear specimens were adequately monitored using our small CNP-PEG-GOxladen contact lenses.

TABLE 1

| | 0.2 mM glucose | | | 0.4 mM glucose | | | 0.6 mM glucose | | |
|---|---|---|---|---|---|---|---|---|---|
| | Before incubation | After incubation | Δ | Before incubation | After incubation | Δ | Before incubation | After incubation | Δ |
| Normalized r | 27.9 ± 0.3 | 28.0 ± 0.1 | 0.3 ± 0.3 | 28.0 ± 0.5 | 28.6 ± 0.5 | 0.34 ± 0.22 | 28.1 ± 0.4 | 28.8 ± 0.3 | 0.6 ± 0.3 |
| Normalized g | 42.6 ± 0.3 | 42.9 ± 0.1 | 0.6 ± 0.1 | 42.6 ± 0.3 | 43.4 ± 0.4 | 0.61 ± 0.21 | 43.0 ± 0.4 | 44.2 ± 1.0 | 1.3 ± 0.3 |
| Normalized b | 29.5 ± 0.6 | 29.1 ± 0.2 | 0.7 ± 0.2 | 29.5 ± 0.6 | 28.1 ± 0.2 | 1.2 ± 0.35 | 29.0 ± 0.7 | 27.4 ± 0.6 | 1.7 ± 0.3 |

Finally, we measured the tear glucose concentrations in specimens from diabetic and nondiabetic human volunteers using the CNP-PEG-GOx-laden contact lenses and a glucose assay kit (FIGS. 30A and 30B). As measured using the CNP-PEG-GOx laden contact lenses, the tear glucose concentrations from diabetic and nondiabetic volunteers were 1.0±0.1 and 0.5±0.1 mM, respectively. As measured by the glucose assay kit, the tear glucose concentrations from diabetic and nondiabetic volunteers were 0.90±0.17 and 0.30±0.06 mM, respectively.

To confirm the pattern of the tear glucose concentration from diabetic and nondiabetic volunteers, their blood glucose concentrations were measured using the general fingerprick method (FIG. 30C). The blood glucose concentrations from diabetic and nondiabetic volunteers were 232.3±26.5 and 99.1±3.4 mg/dL, respectively. Noninvasive prediction of diabetes mellitus in the human volunteers was carried out by analyzing the results from the contact lenses (Table 2) while completely blinded to the conditions of the volunteers. As a result, the status (diabetes or healthy) of the human volunteers was well predicted, except for volunteer no. 3. Also, the tear glucose level in volunteer no. 5 was judged to be from a nondiabetic person, though it was higher than the normal level (<0.6 mM), in accordance with a high blood glucose level at the time of tear collection.

TABLE 2

| Volunteer No. | Status | Sex | Age | Blood glucose (mg/dl) | Tear glucose by lens (mM) | Noninvasive prediction* |
|---|---|---|---|---|---|---|
| 1 | Healthy | Female | 56 | 101 | 0.11 | normoglycemia |
| 2 | Healthy | Female | 28 | 96 | 0.35 | normoglycemia |
| 3 | Healthy | Male | 33 | 95 | 0.80 | hyperglycemia[3] |
| 4 | Healthy | Male | 33 | 88 | 0.44 | normoglycemia |
| 5 | Healthy | Male | 33 | 117[1] | 0.77 | hyperglycemia[2] |
| 6 | Diabetic | Female | 49 | 304 | 1.01 | hyperglycemia |
| 7 | Diabetic | Female | 58 | 244 | 0.66 | hyperglycemia |

TABLE 2-continued

| Volunteer No. | Status | Sex | Age | Blood glucose (mg/dl) | Tear glucose by lens (mM) | Noninvasive prediction* |
|---|---|---|---|---|---|---|
| 8 | Diabetic | Male | 44 | 119 | 0.65 | hyperglycemia |
| 9 | Diabetic | Female | 59 | 299 | 1.05 | hyperglycemia |
| 10 | Diabetic | Male | 59 | 159 | 0.84 | hyperglycemia |

*Blind specimen test was carried out by two researchers in each institute.
[1]Blood glucose was relatively high at the time of sampling, although the physician judged the volunteer to be healthy.
[2]Contact lens predicted hyperglycemia because blood glucose was relatively high at the time of sampling.
[3]Contact lens predicted hyperglycemia although the volunteer was healthy.

What is claimed is:

1. A contact lens-type sensor for detecting glucose, comprising a complex for detecting glucose, the complex comprising cerium oxide ($CeO_2$) nanoparticles and glucose oxidase, wherein the complex is entrapped within the contact lens-type sensor.

2. The contact lens-type sensor according to claim 1, wherein the complex is prepared by sequentially conjugating the cerium oxide nanoparticles, a biocompatible polymer and the glucose oxidase.

3. The contact lens-type sensor according to claim 2, wherein the biocompatible polymer is polyethylene glycol, poly(acrylamide), poly(allylamine), poly(ethyleneimine), poly(amidoamine), polylysine, poly(lactide), poly(acrylic acid), poly(N-isopropylacrylamide), poly(2-(dimethylamino)ethyl methacrylate, poly(caprolactone), chitosan, poly(N-vinyl caprolactam), dextran, poly(styrene sulfate) and poly(vinyl sulfonic acid).

4. The contact lens-type sensor according to claim 2, wherein the sequential conjugation between the cerium oxide nanoparticles, the biocompatible polymer, and the glucose oxidase is formed by a covalent bond.

5. The contact lens-type sensor according to claim 4, wherein the covalent bond is an amide bond.

6. The contact lens-type sensor according to claim 1, wherein the contact lens is made of a biocompatible polymer selected from the group consisting of 2-hydroxyethyl methacrylate, N-vinyl pyrrolidone, methacrylate, methyl methacrylate, and vinyl pyrrolidone.

7. The contact lens-type sensor according to claim 1, wherein the complex is included at 0.3 to 2.5 wt % (w/v) with respect to the total volume of the contact lens-type sensor.

8. A method for detecting glucose, comprising administering the contact lens-type sensor of claim 1 to a subject or treating a subject therewith.

* * * * *